(12) United States Patent
Ishidoh et al.

(10) Patent No.: US 9,402,907 B2
(45) Date of Patent: Aug. 2, 2016

(54) PHARMACEUTICAL COMPOSITION CONTAINING DIAMINE DERIVATIVE

(75) Inventors: Koichi Ishidoh, Kanagawa (JP); Kazuhiro Matsuura, Kanagawa (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/237,884

(22) PCT Filed: Aug. 9, 2012

(86) PCT No.: PCT/JP2012/070314
§ 371 (c)(1),
(2), (4) Date: Feb. 9, 2014

(87) PCT Pub. No.: WO2013/022059
PCT Pub. Date: Feb. 14, 2013

(65) Prior Publication Data
US 2014/0171464 A1    Jun. 19, 2014

(30) Foreign Application Priority Data
Aug. 10, 2011   (JP) ................. 2011-174946

(51) Int. Cl.
| | | |
|---|---|---|
| *A61K 47/26* | (2006.01) | |
| *A61K 47/14* | (2006.01) | |
| *A61K 47/22* | (2006.01) | |
| *A61K 31/437* | (2006.01) | |
| *A61K 47/12* | (2006.01) | |
| *A61K 9/20* | (2006.01) | |
| *A61K 9/48* | (2006.01) | |
| *A61K 31/444* | (2006.01) | |

(52) U.S. Cl.
CPC ............... *A61K 47/26* (2013.01); *A61K 9/2077* (2013.01); *A61K 9/4808* (2013.01); *A61K 31/437* (2013.01); *A61K 31/444* (2013.01); *A61K 47/12* (2013.01); *A61K 47/14* (2013.01); *A61K 47/22* (2013.01)

(58) Field of Classification Search
None
See application file for complete search history.

(56) References Cited

U.S. PATENT DOCUMENTS 4,361,545 A    11/1982   Powell et al.
4,582,570 A    4/1986    Mix
(Continued)

FOREIGN PATENT DOCUMENTS

CA    2434976      8/2002
CN    101652139    2/2010
(Continued)

OTHER PUBLICATIONS

International Search Report, issued in PCT/JP2010/060261, mailed Sep. 21, 2010.
(Continued)

*Primary Examiner* — San-Ming Hui
*Assistant Examiner* — Andrew Lee
(74) *Attorney, Agent, or Firm* — Locke Lord LLP

(57) ABSTRACT

An object of the present invention is to provide a pharmaceutical composition containing compound I or a pharmacologically acceptable salt thereof, or a solvate thereof as an active ingredient, which is favorably dissolved in the neutral region. The present invention relates to a pharmaceutical composition containing (A) $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide or a pharmacologically acceptable salt thereof, or a solvate thereof, and (B) an acid or a salt thereof.

16 Claims, 19 Drawing Sheets

(56) References Cited

U.S. PATENT DOCUMENTS

| | | | |
|---|---|---|---|
| 5,055,600 | A | 10/1991 | Wagner |
| 5,091,191 | A | 2/1992 | Oda et al. |
| 5,202,129 | A | 4/1993 | Samejima et al. |
| 5,677,469 | A | 10/1997 | Van Eikeren et al. |
| 5,958,453 | A | 9/1999 | Ohno et al. |
| 7,081,256 | B2 | 7/2006 | Kubota et al. |
| 7,192,968 | B2 | 3/2007 | Yoshino et al. |
| 7,342,014 | B2 | 3/2008 | Ohta et al. |
| 7,365,205 | B2 | 4/2008 | Ohta et al. |
| 7,547,786 | B2 | 6/2009 | Nagasawa et al. |
| 7,576,135 | B2 | 8/2009 | Ohta et al. |
| 7,605,180 | B2 | 10/2009 | Ninomiya et al. |
| 7,674,904 | B2 | 3/2010 | Doshan et al. |
| 2002/0160048 | A1 | 10/2002 | Bechtold-Peters et al. |
| 2003/0086972 | A1 | 5/2003 | Appel et al. |
| 2004/0052845 | A1 | 3/2004 | Appel et al. |
| 2005/0020645 | A1 | 1/2005 | Ohta et al. |
| 2005/0119486 | A1 | 6/2005 | Ohta et al. |
| 2005/0245565 | A1 | 11/2005 | Ohta et al. |
| 2006/0252837 | A1 | 11/2006 | Ohta et al. |
| 2006/0275357 | A1 | 12/2006 | Oomura et al. |
| 2007/0135476 | A1 | 6/2007 | Nagasawa et al. |
| 2008/0015215 | A1 | 1/2008 | Ohta et al. |
| 2009/0105491 | A1 | 4/2009 | Sato et al. |
| 2009/0192313 | A1 | 7/2009 | Nagasawa et al. |
| 2009/0270446 | A1 | 10/2009 | Ohta et al. |
| 2009/0281074 | A1 | 11/2009 | Ohta et al. |
| 2010/0081685 | A1* | 4/2010 | Kojima et al. ............... 514/301 |
| 2011/0045028 | A1 | 2/2011 | Iinuma et al. |
| 2011/0229567 | A1* | 9/2011 | Hirata et al. ............... 424/464 |
| 2012/0114711 | A1 | 5/2012 | Kamada |
| 2013/0004550 | A1 | 1/2013 | Kanamaru et al. |
| 2013/0005763 | A1 | 1/2013 | Kanamaru et al. |
| 2013/0012535 | A1 | 1/2013 | Kanamaru et al. |
| 2013/0022683 | A1 | 1/2013 | Kamada |
| 2013/0337064 | A1 | 12/2013 | Kojima |

FOREIGN PATENT DOCUMENTS

| | | |
|---|---|---|
| CN | 102058889 | 5/2011 |
| EP | 1103253 | 5/2001 |
| EP | 1 270 006 | 1/2003 |
| EP | 2140867 | 1/2010 |
| JP | H02-704 | 1/1990 |
| JP | H08-73345 | 3/1996 |
| JP | H09-309829 | 12/1997 |
| JP | 2001-151672 | 6/2001 |
| JP | 2003-73274 | 3/2003 |
| JP | 2004-505907 | 2/2004 |
| JP | 2004-518710 | 6/2004 |
| JP | 2005-263816 | 9/2005 |
| RU | 2 271 805 | 8/2004 |
| WO | 02/064124 | 8/2002 |
| WO | 03/000657 | 1/2003 |
| WO | 03/000680 | 1/2003 |
| WO | 03/016302 | 2/2003 |
| WO | 03/070279 | 8/2003 |
| WO | 03/097102 | 11/2003 |
| WO | 2004/058715 | 7/2004 |
| WO | 2004/110448 | 12/2004 |
| WO | 2005/047296 | 5/2005 |
| WO | 2007/032498 | 3/2007 |
| WO | 2008/066102 | 6/2008 |
| WO | 2008/129846 | 10/2008 |
| WO | 2008/156159 | 12/2008 |
| WO | 2011/102504 | 8/2011 |
| WO | 2011/102505 | 8/2011 |
| WO | 2011/102506 | 8/2011 |
| WO | 2011/115067 | 9/2011 |

OTHER PUBLICATIONS

Written Opinion of the International Searching Authority, issued in PCT/JP2010/060261, mailed Sep. 21, 2010.
International Preliminary Report on Patentability, issued in PCT/JP2010/060261, mailed Dec. 20, 2011.
International Search Report, issued in PCT/JP2011/055956, mailed Apr. 26, 2011.
Written Opinion of the International Searching Authority, issued in PCT/JP2011/055956, mailed Apr. 26, 2011.
International Preliminary Report on Patentability, issued in PCT/JP2011/055956, mailed Oct. 23, 2012.
International Search Report, issued in PCT/JP2012/070314, mailed Oct. 23, 2012.
Written Opinion of the International Searching Authority, issued in PCT/JP2012/070314, mailed Oct. 23, 2012.
International Preliminary Report on Patentability, issued in PCT/JP2012/070314, mailed Feb. 11, 2014.
International Search Report, issued in PCT/JP2008/000791, mailed Jun. 24, 2008.
Written Opinion of the International Searching Authority, issued in PCT/JP2008/000791, mailed Jun. 24, 2008.
International Preliminary Report on Patentability, issued in PCT/JP2008/000791, mailed Oct. 20, 2009.
Extended Search Report, issued in European Patent Application No. 08720658.7, mailed Jun. 3, 2013.
Turpie, A. G.G., "Oral, Direct Factor Xa Inhibitors in development for the prevention and Treatment of Thromboembolic Diseases," Arteriosclerosis, Thrombosis, and Vascular Biology, vol. 27, No. 6, pp. 1238-1247, XP002672841, Mar. 22, 2007.
Jacob, et al. "Novel Co-Processed Excipients of Mannitol and Microcrystalline Cellulose for Preparing Fast Dissolving Tablets of Glipizide," Indian Journal of Pharmaceutical Sciences, pp. 633-639, Sep. 1, 2007.
Shin-Etsu Chemical Co., Ltd., Pharmacoat, "Film Coating Material and Binder," pp. 1-12, Feb. 2005.
Serajuddin, A.T.M., "Salt formation to improve drug solubility" Advanced Drug Delivery Reviews, vol. 59, pp. 603-616, May 2007.
Nassab, et al., "Physicochemical characterization of meloxicam-mannitol binary system," Journal of Pharmaceutical and Biomedical Analysis 41:1191-1197, (2006).
Takeuchi, et al., "Tabletting of solid dispersion particles consisting of indomethacin and porous silica particles," Chem., Pharm., Bull., 53(5) 487-491 (2005).
Gombas, et al., "Study of Thermal Behaviour of Sugar Alcohols," Journal of Thermal Analysis and Calorimetry, vol. 73, pp. 615-621 (2003).
Jiho, Inc., "Handbook for new drug Approval Application 1993," pp. 128-133 (with partial English translation) (1993).
Chowdary, et al., "Effect of Selected Binders and Disintergrants on the Dissolution Rate Nimesulide from Tablets," Indian Journal of Pharmaceutical Sciences, vol. 62, Issue 3, pp. 224-228, Jun. 2000.
Chinese Search Report, issued in Chinese Application No. 2012800388139, dated Dec. 17, 2014.
Hylek, E.M., "Drug evaluation: DU-176b, an oral, direct Factor Xa antagonist." Current Opinion in Investigational Drugs, 8, (9), 778-783 (2007).
Furugohri, T., et al., "DU-176b, A potent and orally active factor Xa inhibitor: In vitro and in vivo pharmacological profiles" Journal of Thrombosis and Haemostasis, 6(9), 1542-1549 (2008).
Supplementary European Search Report issued in corresponding European Application EP12822801, dated May 8, 2015.
Mitchell, S.A., et al., "A compaction process to enhance dissolution of poorly water-soluble drugs using hydroxypropyl methylcellulose"; Int. J. Pharm., 250(1): 3-11 (2003).
Vippagunta, S.R., et al., "Crystalline solids"; Advanced Drug Delivery Reviews; 48:3-26 (2001).
Braga, D., et al., "Crystal polymorphism and multiple crystal forms"; Struct. Bond, 132:25-50 (2009).
Mueller, U., "Inorganic Structural Chemistry"; pp. 14-15, section 3.1—Polymorphism, (1993).
Gerhardt, A.H., "Moisture effects on solid dosage forms—Formulation, Processing, and Stability": J. of GXP Compliance, 13(1):58-66 (2009).

* cited by examiner

PHARMACEUTICAL COMPOSITION CONTAINING DIAMINE DERIVATIVE

This application is a national phase entry under 35 U.S.C. §371 of International Application Number PCT/JP2012/070314, filed on Aug. 9, 2012, entitled "PHARMACEUTICAL COMPOSITION CONTAINING DIAMINE DERIVATIVE", which claims the benefit of Japanese Patent Application Number JP 2011-174946, filed on Aug. 10, 2011, all of which are hereby incorporated by reference.

BACKGROUND OF THE INVENTION

1. Field of the Invention

The present invention relates to a pharmaceutical composition that is improved in its dissolution property, containing a compound that exhibits an inhibitory effect on activated blood coagulation factor X, and that is useful as a preventative and/or therapeutic drug for thrombotic diseases.

2. Description of Related Art $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

[Formula 1]

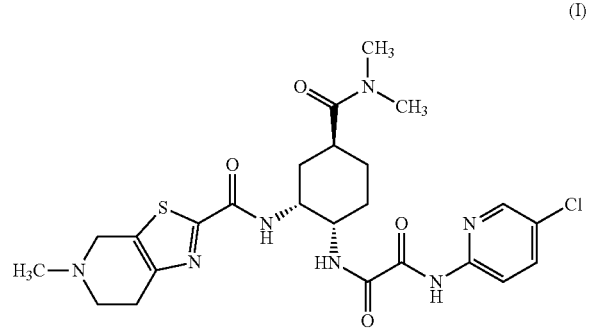

(I)

(in the present specification, the compound represented by formula (I) is also referred to as compound I) or a pharmacologically acceptable salt thereof, or a solvate thereof is known to exhibit an inhibitory effect on activated blood coagulation factor X (hereinafter, also referred to as FXa in the present specification) and be useful as a pharmaceutical drug, particularly, an activated blood coagulation factor X inhibitor (hereinafter, also referred to as an FXa inhibitor or anti-FXa in the present specification) and/or an agent for preventing and/or treating thrombosis or embolism (Patent Documents 1 to 6).

Compound I is a basic compound that exhibits favorable solubility in a strongly acidic aqueous solution, but reduced solubility in an aqueous solution having a pH in the neutral region (e.g., a neutral buffer). Therefore, a solid formulation containing compound I or a pharmacologically acceptable salt thereof, or a solvate thereof as an active ingredient exhibits a poor dissolution property of compound I or the pharmacologically acceptable salt thereof, or the solvate thereof in an aqueous solution having a pH in the neutral region. Methods for improving the dissolution rate of the active ingredient, comprising preparing a composition containing compound I combined with a sugar alcohol and/or a water-swelling additive (Patent Document 4), comprising coating a composition containing compound I with one or two or more coating agents selected from a cellulose derivative, a polyvinyl compound, an acrylic acid derivative, and a saccharide (Patent Document 4), or comprising adjusting the proportion of compound I or a pharmacologically acceptable salt thereof, or a solvate thereof in a pharmaceutical composition (Patent Document 5) are known as methods for improving such dissolution property in the neutral region of a solid formulation containing compound I or a pharmacologically acceptable salt thereof, or a solvate thereof as an active ingredient. Alternatively, it is known that the dissolution property in the neutral region of a solid formulation containing compound I or a pharmacologically acceptable salt thereof, or a solvate thereof as an active ingredient is improved by producing a granulated material containing compound I for use in the formulation under conditions for keeping the maximum water content of the granulated material during granulation at 10% or less (Patent Document 6).

Also, a sustained release formulation containing compound I is known as a formulation containing compound I (Patent Documents 7 to 9).

CITATION LIST

Patent Documents

Patent Document 1: WO 2003/000657
Patent Document 2: WO 2003/000680
Patent Document 3: WO 2003/016302
Patent Document 4: WO 2008/129846
Patent Document 5: WO 2010/147169
Patent Document 6: WO 2011/115067
Patent Document 7: WO 2011/102504
Patent Document 8: WO 2011/102505
Patent Document 9: WO 2011/102506

BRIEF SUMMARY OF THE INVENTION

Technical Problem

An object of the present invention is to provide a pharmaceutical composition containing compound I or a pharmacologically acceptable salt thereof, or a solvate thereof as an active ingredient, which is favorably dissolved in the neutral region.

Solution to Problem

As a result of studying the dissolution property of a solid formulation comprising compound I or a pharmacologically acceptable salt thereof, or a solvate thereof, the present inventors have found that upon exposure to an aqueous solution having a pH higher than the neutral region, such a formulation forms a gel-like structure, resulting in delayed dissolution of the drug contained in the formulation. The present inventors further found that the addition of an acid component to the solid formulation comprising compound I or a pharmacologically acceptable salt thereof, or a solvate thereof prevents the formation of this gel-like structure to thereby improve the dissolution property of compound I or the pharmacologically acceptable salt thereof, or the solvate thereof from the formulation. Based on these findings, the present invention has been completed.

Specifically, the present invention relates to:
[1] a pharmaceutical composition containing (A) compound I or a pharmacologically acceptable salt thereof, or a solvate thereof, and (B) an acid or a salt thereof;

[2] the pharmaceutical composition according to [1], wherein the component (B) is an organic acid or a salt thereof;
[3] the pharmaceutical composition according to [1], wherein the component (B) is an organic acid or a salt thereof which is solid at room temperature;
[4] the pharmaceutical composition according to [1], wherein the component (B) is a carboxylic acid or an enol, or a salt thereof;
[5] the pharmaceutical composition according to [1], wherein the component (B) is a carboxylic acid or a salt thereof;
[6] the pharmaceutical composition according to [1], wherein the component (B) is an enol or a salt thereof;
[7] the pharmaceutical composition according to [1], wherein the component (B) is a carboxylic acid or a salt thereof which is solid at room temperature;
[8] the pharmaceutical composition according to [1], wherein the component (B) is one or more components selected from the group consisting of ethyl acrylate-methyl methacrylate copolymer dispersion, adipic acid, sodium hydrogensulfite, ascorbic acid, sodium ascorbate, aspartic acid, alginic acid, erythorbic acid, sodium erythorbate, hydrochloric acid, a carboxyvinyl polymer, sodium carboxymethyl starch, carmellose, carmellose potassium, carmellose calcium, carmellose sodium, citric acid, croscarmellose sodium, succinic acid, monosodium succinate, acetic acid, calcium acetate, a vinyl acetate resin, tartaric acid, potassium hydrogentartrate, sodium tartrate, sorbic acid, potassium sorbate, hydroxypropyl methylcellulose acetate succinate, fumaric acid, monosodium fumarate, stearyl sodium fumarate, maleic acid, malonic acid, anhydrous sodium sulfate, methacrylic acid copolymer L, methacrylic acid copolymer LD, malic acid, phosphoric acid, potassium dihydrogenphosphate, and sodium dihydrogenphosphate;
[9] the pharmaceutical composition according to [1], wherein the component (B) is one or more components selected from the group consisting of adipic acid, ascorbic acid, sodium ascorbate, aspartic acid, alginic acid, a carboxyvinyl polymer, sodium carboxymethyl starch, carmellose, carmellose potassium, carmellose calcium, carmellose sodium, citric acid, croscarmellose sodium, succinic acid, tartaric acid, potassium hydrogentartrate, sodium tartrate, hydroxypropyl methylcellulose acetate succinate, fumaric acid, monosodium fumarate, stearyl sodium fumarate, maleic acid, malonic acid, methacrylic acid copolymer L, and malic acid;
[10] the pharmaceutical composition according to [1], wherein the component (B) is one or more components selected from the group consisting of ascorbic acid, sodium carboxymethyl starch, carmellose, carmellose potassium, carmellose calcium, croscarmellose sodium, fumaric acid, and stearyl sodium fumarate;
[11] the pharmaceutical composition according to [1], which is a solid formulation;
[12] the pharmaceutical composition according to [1], which is a tablet or a capsule;
[13] the pharmaceutical composition according to [12], which is an immediate release tablet or capsule;
[14] the pharmaceutical composition according to [12], which comprises the component (A) and the component (B) within granules; and
[15] the pharmaceutical composition according to [12], which comprises the component (A) within granules and comprises the component (B) outside the granules.

Advantageous Effects of Invention

The present invention provides a pharmaceutical composition containing compound I or a pharmacologically acceptable salt thereof, or a solvate thereof and having a favorable dissolution property in the neutral range. The pharmaceutical composition of the present invention further has such an excellent feature that the pharmaceutical composition exhibits a favorable dissolution property regardless of the density of a tablet.

DETAILED DESCRIPTION OF THE INVENTION

Figure 1A:
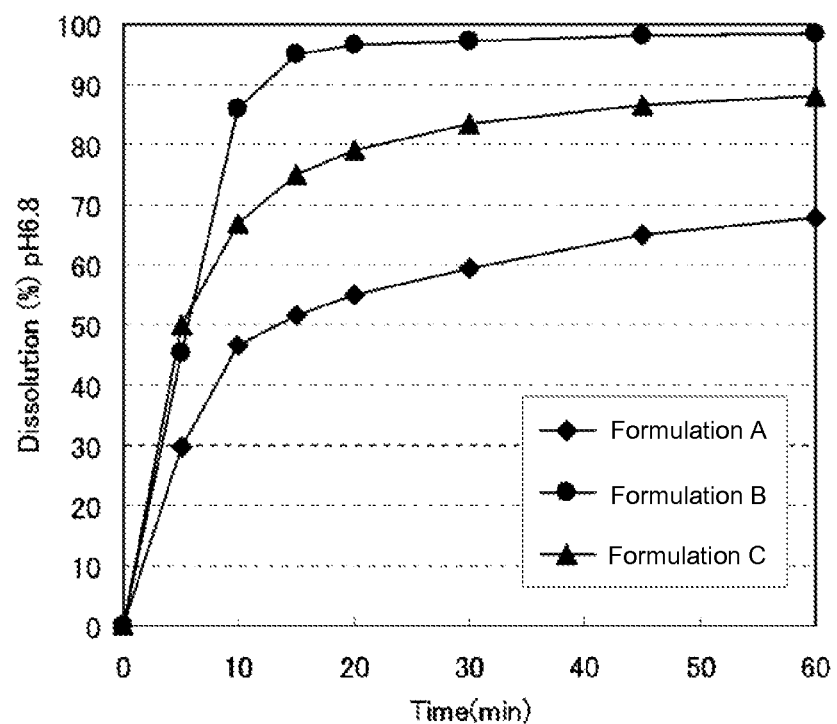
FIG. 1A is a diagram showing the dissolution property of compound I in the neutral range for uncoated tablets having formulations A to C. The vertical axis shows the dissolution amount of compound I, and the horizontal axis shows time (min).

In the present specification, "acid" refers to a compound which exhibits acidity and can be added to pharmaceuticals, and encompasses organic acids and inorganic acids.

In the present specification, "organic acid" refers to an organic compound which exhibits acidity and may be used as an additive for pharmaceuticals. Examples of organic acids include carboxylic acids, sulfonic acids, and enols.

In the present specification, "acidity" refers to a pH (hydrogen ion exponent) smaller than 7. "Neutrality" refers to a pH of 7.

The "neutral region" employed in relation to the dissolution property of the pharmaceutical composition of the present invention refers to a pH range of 6 or higher and 8 or lower.

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (compound I) represented by the following formula (I):

[Formula 2]

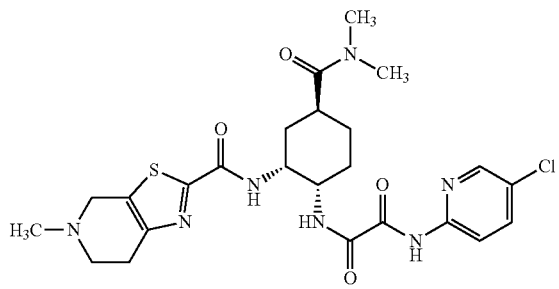

(I)

is called edoxaban (N-(5-chloropyridin-2-yl)-N'-[(1S,2R,4S)-4-(N,N-dimethylcarbamoyl)-2-(5-methyl-4,5,6,7-tetrahydro[1,3]thiazolo[5,4-c]pyridine-2-carboxamido)cyclohexyl]oxamide) as International Nonproprietary Name (INN).

Compound I may be a solvate (including hydrates) or may be a pharmacologically acceptable salt or a solvate (including hydrates) of the salt.

Examples of the salt of compound I include hydrochloride, sulfate, hydrobromide, citrate, hydroiodide, phosphate, nitrate, benzoate, methanesulfonate, benzenesulfonate, 2-hydroxyethanesulfonate, p-toluenesulfonate, acetate, propionate, oxalate, malonate, succinate, glutarate, adipate, tartrate, maleate, fumarate, malate, and mandelate.

The salt of compound I is preferably hydrochloride, tartrate, or p-toluenesulfonate, particularly preferably p-toluenesulfonate.

Preferred examples of compound I or a pharmacologically acceptable salt thereof, or a solvate thereof can include the following compounds:

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate; and $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (Ia):

[Formula 3]

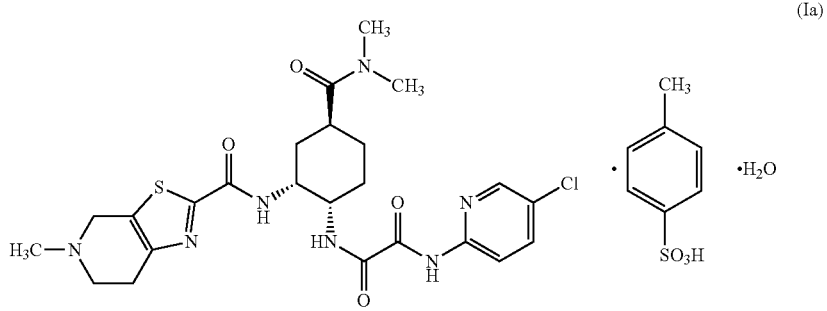

(in the present specification, the compound represented by formula (Ia) is also referred to as compound Ia).

The compound I or a pharmacologically acceptable salt thereof, or a solvate thereof can be produced by a method described in Patent Documents 1 to 3 or a method equivalent thereto.

The efficacy and safety of pharmaceutical compositions for oral administration such as tablets are largely influenced by the dissolution property of the active ingredient(s). Thus, the criteria regarding the dissolution property are defined in each country. For example, in Japan, the USA, and Europe, the pharmacopoeia specifies a method for a dissolution test. In the dissolution test, various dissolution media are used. These dissolution media are adjusted to a pH range of 1 to 8. For example, strongly acidic dissolution media (e.g., JP 1st fluid described in the Japanese Pharmacopoeia and 0.1 N hydrochloric acid solutions), dissolution media of pH 3 to 5 (e.g., acetic acid-sodium acetate buffers and McIlvaine buffer), dissolution media of pH 6.8 (e.g., JP 2nd fluid described in the Japanese Pharmacopoeia and phosphate buffers of pH 6.8), and water are shown as the dissolution media in the pharmacopoeia or the like of each country. Formulations for oral administration are required to have a favorable dissolution property in dissolution tests using these dissolution media.

Compound I is a basic compound that exhibits favorable solubility in a strongly acidic aqueous solution, but reduced solubility in an aqueous solution in the neutral range (neutral buffer, etc.). Therefore, a pharmaceutical composition containing compound I or a pharmacologically acceptable salt thereof, or a solvate thereof also exhibits a poor dissolution property of compound I or the pharmacologically acceptable salt thereof, or the solvate thereof in an aqueous solution having a pH in the neutral region.

One of the features of the present invention is to enhance the dissolution rate in the neutral region of a pharmaceutical composition containing compound I or a pharmacologically acceptable salt thereof, or a solvate thereof by formulating the pharmaceutical composition containing compound I or a pharmacologically acceptable salt thereof, or a solvate thereof with an acid or a salt thereof. The acid employed in the pharmaceutical composition of the present invention refers to a compound which exhibits acidity and can be added to pharmaceuticals. Examples of the acid include inorganic acids and organic acids (e.g., carboxylic acids, enols, and sulfonic acids).

Examples of the organic acid or the salt thereof which is solid at room temperature, employed in the pharmaceutical composition of the present invention include adipic acid, aspartic acid, alginic acid, benzoic acid, carboxyvinyl polymers, carmellose, citric acid, glutamic acid, succinic acid, tartaric acid, sorbic acid, hydroxypropyl methylcellulose acetate succinate, fumaric acid, maleic acid, malonic acid, anhydrous citric acid, methacrylic acid copolymers, malic acid, ascorbic acid, erythorbic acid, sodium L-aspartate, sodium benzoate, sodium carboxymethyl starch, carmellose potassium, carmellose calcium, carmellose sodium, sodium dihydrogencitrate, disodium citrate, calcium gluconate, sodium L-glutamate, croscarmellose sodium, monosodium succinate, calcium acetate, vinyl acetate resins, sodium tartrate, potassium hydrogentartrate, potassium sorbate, calcium lactate, monosodium fumarate, stearyl sodium fumarate, anhydrous sodium citrate, sodium malate, sodium ascorbate, and sodium erythorbate. Preferred examples thereof include adipic acid, aspartic acid, alginic acid, carboxyvinyl polymers, carmellose, citric acid, tartaric acid, hydroxypropyl methylcellulose acetate succinate, fumaric acid, maleic acid, malonic acid, methacrylic acid copolymers, malic acid, ascorbic acid, sodium carboxymethyl starch, carmellose potassium, carmellose calcium, carmellose sodium, croscarmellose sodium, stearyl sodium fumarate, ascorbic acid, and sodium ascorbate. More preferred examples thereof include carmellose, fumaric acid, carmellose potassium, carmellose calcium, carmellose sodium, croscarmellose sodium, stearyl sodium fumarate, ascorbic acid, and sodium ascorbate.

No particular limitation is imposed on the inorganic acid employed in the pharmaceutical composition of the present invention, so long as the inorganic acid can be added to pharmaceuticals. Examples of the inorganic acid include hydrochloric acid and phosphoric acid.

No particular limitation is imposed on the salt of the inorganic acid employed in the pharmaceutical composition of the present invention, so long as the salt of the inorganic acid can be added to pharmaceuticals. Examples of the salt of the inorganic acid include sodium hydrogensulfite, potassium dihydrogenphosphate, and sodium dihydrogenphosphate.

No particular limitation is imposed on the carboxylic acid employed in the pharmaceutical composition of the present invention, so long as the carboxylic acid can be added to pharmaceuticals. Examples of the carboxylic acid include ethyl acrylate-methyl methacrylate copolymer dispersion, adipic acid, aspartic acid, alginic acid, benzoic acid, carboxyvinyl polymers, carmellose, citric acid, glutamic acid, succinic acid, acetic acid, tartaric acid, sorbic acid, lactic acid, hydroxypropyl methylcellulose acetate succinate, fumaric acid, maleic acid, malonic acid, anhydrous citric acid, methacrylic acid copolymers, and malic acid. Preferred examples thereof include adipic acid, aspartic acid, alginic acid, carboxyvinyl polymers, carmellose, citric acid, tartaric acid, hydroxypropyl methylcellulose acetate succinate, fumaric acid, maleic acid, malonic acid, methacrylic acid copolymers, and malic acid. More preferred examples thereof include carmellose and fumaric acid.

No particular limitation is imposed on the salt of the carboxylic acid (carboxylate) employed in the pharmaceutical composition of the present invention, so long as the carboxylate can be added to pharmaceuticals. Examples of the carboxylate include sodium aspartate, sodium L-aspartate, sodium benzoate, sodium carboxymethyl starch, carmellose potassium, carmellose calcium, carmellose sodium, sodium dihydrogencitrate, disodium citrate, calcium gluconate, sodium L-glutamate, croscarmellose sodium, monosodium succinate, calcium acetate, vinyl acetate resins, sodium tartrate, potassium hydrogentartrate, potassium sorbate, calcium lactate, monosodium fumarate, stearyl sodium fumarate, anhydrous sodium citrate, and sodium malate. Preferred examples thereof include sodium carboxymethyl starch, carmellose potassium, carmellose calcium, carmellose sodium, croscarmellose sodium, and stearyl sodium fumarate. More preferred examples thereof include carmellose potassium, carmellose calcium, croscarmellose sodium, and stearyl sodium fumarate.

No particular limitation is imposed on the enol employed in the pharmaceutical composition of the present invention, so long as the enol can be added to pharmaceuticals. Examples of the enol include ascorbic acid and erythorbic acid. Preferred examples thereof include ascorbic acid.

No particular limitation is imposed on the salt of the enol employed in the pharmaceutical composition of the present invention, so long as the salt of the enol can be added to pharmaceuticals. Examples of the salt of the enol include sodium ascorbate and sodium erythorbate. Preferred examples thereof include sodium ascorbate.

Examples of the carboxylic acid or the salt thereof which is solid at room temperature, employed in the pharmaceutical composition of the present invention include adipic acid, aspartic acid, alginic acid, benzoic acid, carboxyvinyl polymers, carmellose, citric acid, glutamic acid, succinic acid, tartaric acid, sorbic acid, hydroxypropyl methylcellulose acetate succinate, fumaric acid, maleic acid, malonic acid, anhydrous citric acid, methacrylic acid copolymers, malic acid, sodium L-aspartate, sodium benzoate, sodium carboxymethyl starch, carmellose potassium, carmellose calcium, carmellose sodium, sodium dihydrogencitrate, disodium citrate, calcium gluconate, sodium L-glutamate, croscarmellose sodium, monosodium succinate, calcium acetate, vinyl acetate resins, sodium tartrate, potassium hydrogentartrate, potassium sorbate, calcium lactate, sodium fumarate, stearyl sodium fumarate, anhydrous sodium citrate, and sodium malate. Preferred examples thereof include adipic acid, aspartic acid, alginic acid, carboxyvinyl polymers, carmellose, citric acid, tartaric acid, hydroxypropyl methylcellulose acetate succinate, fumaric acid, maleic acid, malonic acid, methacrylic acid copolymers, malic acid, sodium carboxymethyl starch, carmellose potassium, carmellose calcium, carmellose sodium, croscarmellose sodium, and stearyl sodium fumarate. More preferred examples thereof include carmellose, fumaric acid, carmellose potassium, carmellose calcium, carmellose sodium, croscarmellose sodium, and stearyl sodium fumarate.

The amount of the acid or the salt thereof contained in the pharmaceutical composition of the present invention is not particularly limited and can be determined appropriately by those skilled in the art using the dissolution test method and the dissolution criteria described in the present specification so that the pharmaceutical composition exhibits the desired dissolution property. The amount of the acid component contained in the pharmaceutical composition of the present invention is not particularly limited, and however, the acid component is contained in an amount of 0.1% by weight to 80% by weight, 0.1% by weight to 70% by weight, 0.1% by weight to 60% by weight, 0.1% by weight to 50% by weight, 0.1% by weight to 40% by weight, 0.1% by weight to 30% by weight, 0.1% by weight to 20% by weight, or 0.1% by weight to 10% by weight, preferably in an amount of 1% by weight to 50% by weight, 1% by weight to 40% by weight, 1% by weight to 30% by weight, 1% by weight to 20% by weight, or 1% by weight to 10% by weight, more preferably in an amount of 1% by weight to 20% by weight, 1% by weight to 10% by weight, or 1% by weight to 5% by weight, with respect to, for example, the weight of a tablet.

No particular limitation is imposed on an excipient employed in the pharmaceutical composition of the present invention, so long as the excipient is usually used by those skilled in the art. Preferred examples of the excipient include sugar alcohols, water-swelling additives, and their combinations.

The sugar alcohol is preferably mannitol, erythritol, or xylitol, or the like, particularly preferably mannitol.

The water-swelling additive means an additive for pharmaceuticals which swells with water added thereto. Examples of the water-swelling additive include excipients and bases having water swellability. No particular limitation is imposed on the water-swelling additive employed in the present invention, so long as the water-swelling additive is usually used by those skilled in the art. Examples of the water-swelling additive include pregelatinized starch, gelatinized starch, crystalline cellulose, sodium carboxymethyl starch, carmellose (carboxymethyl cellulose), carmellose calcium, croscarmellose sodium (croscarboxymethyl cellulose sodium), soybean lecithin, low-substituted hydroxypropyl cellulose, tragacanth powder, bentonite, and their combinations. The water-swelling additive is preferably pregelatinized starch or crystalline cellulose, particularly preferably pregelatinized starch.

The solid formulation of the present invention preferably contains a sugar alcohol in an amount of 0.01 to 99.0 wt. %, preferably 20 to 80 wt. %, more preferably 40 to 60 wt. %. Also, the solid formulation of the present invention preferably contains a water-swelling additive in an amount of 0.01 to 90 wt. %, preferably 0.1 to 80 wt. %, more preferably 5 to 50 wt. %. In the case where the solid formulation contains the water-swelling additive and sugar alcohol, the ratio of water-swelling additive to sugar alcohol in the formulation is preferably 0.05 to 50 parts by weight (sugar alcohol) to 1 part by weight (water-swelling additive), more preferably 1 to 10 parts by weight (sugar alcohol), particularly preferably 1.5 to 4 parts by weight (sugar alcohol).

In addition to the acid or the salt thereof and the sugar alcohol and/or the water-swelling additive, the pharmaceutical composition of the present invention may comprise a water-soluble excipient other than the sugar alcohol, a water-insoluble excipient, a pH adjuster, a disintegrant, a binder, a lubricant, a fluidizing agent, a coloring agent, a polishing agent, etc.

Examples of water-soluble excipients include, but are not limited to: saccharides such as fructose, purified sucrose, sucrose, purified sucrose spherical granules, lactose, anhydrous lactose, sucrose-starch spherical granules, semi-digested starch, glucose, glucose hydrate, pullulan, and β-cyclodextrin; and aminoethylsulfonic acid, sodium chloride, citric acid, sodium citrate, glycine, calcium gluconate, L-glutamine, tartaric acid, potassium hydrogentartrate, ammonium carbonate, dextran 40, dextrin, calcium lactate, povidone, macrogol (polyethylene glycol) 1500, macrogol 1540, macrogol 4000, macrogol 6000, anhydrous citric acid, DL-malic acid, sodium hydrogenphosphate, potassium dihydrogenphosphate, and sodium dihydrogenphosphate. The water-soluble excipient is preferably selected from saccharides. Specific examples include purified sucrose, sucrose, lactose, lactose granules, glucose, glucose hydrate, or pullulan. Of these, lactose is more preferred.

Examples of water-insoluble excipients include, but are not limited to, L-aspartic acid, alginic acid, carmellose sodium, hydrous silicon dioxide, crospovidone, calcium glycerophosphate, magnesium silicate aluminate, calcium silicate, magnesium silicate, light anhydrous silicic acid, crystalline cellulose, cellulose powder, synthetic aluminum silicate, synthetic aluminum silicate/hydroxypropyl starch/crystalline cellulose, wheat starch, rice starch, cellulose acetate phthalate, titanium oxide, magnesium oxide, dihydroxyaluminum aminoacetate, calcium tertiary phosphate, talc, calcium carbonate, magnesium carbonate, precipitated calcium carbonate, natural aluminum silicate, corn starch, granulated corn starch, potato starch, hydroxypropyl cellulose, hydroxypropyl starch, calcium hydrogenphosphate anhydrous, granulated calcium hydrogenphosphate anhydrous, or calcium dihydrogenphosphate. Of these, crystalline cellulose or cellulose powder are preferred as a water-insoluble excipient.

Examples of pH adjusters include, but are not limited to, adipic acid, citric acid, calcium citrate, succinic acid, acetic acid, tartaric acid, sodium hydroxide, magnesium hydroxide, sodium hydrogencarbonate, sodium carbonate, lactic acid, calcium lactate, fumaric acid, sodium fumarate, maleic acid, anhydrous citric acid, sodium monohydrogen phosphate anhydrous, and malic acid. Of these, fumaric acid is preferred as a pH adjuster.

Examples of disintegrants include, but are not limited to, adipic acid, alginic acid, gelatinized starch, sodium carboxymethyl starch, carmellose, carmellose calcium, carmellose sodium, hydrous silicon dioxide, calcium citrate, croscarmellose sodium, crospovidone, light anhydrous silicic acid, crystalline cellulose, synthetic aluminum silicate, wheat starch, rice starch, cellulose acetate phthalate, calcium stearate, low-substituted hydroxypropyl cellulose, corn starch, tragacanth powder, potato starch, hydroxyethylmethyl cellulose, hydroxypropyl starch, pregelatinized starch, monosodium fumarate, povidone, anhydrous citric acid, methyl cellulose, or calcium dihydrogenphosphate. Preferably, at least one or more disintegrants contained in the pharmaceutical composition of the present invention are organic acids and/or salts thereof. Examples of preferred disintegrants contained in the pharmaceutical composition of the present invention include carmellose, carmellose calcium, and sodium carboxymethyl starch.

Examples of binders include, but are not limited to, maltose gum arabic, gum arabic powder, sodium alginate, propylene glycol alginate ester, hydrolyzed gelatin powder, hydrolyzed starch-light anhydrous silicic acid, fructose, carboxyvinyl polymer, carboxymethylethyl cellulose, hydrous silicon dioxide, agar powder, light anhydrous silicic acid, light anhydrous silicic acid-containing hydroxypropyl cellulose, crystalline cellulose, synthetic aluminum silicate, high-molecular polyvinylpyrrolidone, copolydone, wheat starch, rice starch, polyvinyl acetate resin, cellulose acetate phthalate, dioctyl sodium sulfosuccinate, dihydroxyaluminum aminoacetate, sodium potassium tartrate, sucrose fatty acid ester, purified gelatin, purified sucrose, gelatin, D-sorbitol, dextrin, starch, corn starch, tragacanth, tragacanth powder, lactose, concentrated glycerin, sucrose, potato starch, hydroxyethylcellulose, hydroxyethylmethyl cellulose, hydroxypropyl cellulose, hydroxypropyl starch, hydroxypropylmethyl cellulose 2208, hydroxypropylmethyl cellulose 2906, hydroxypropylmethyl cellulose 2910, hydroxypropylmethyl cellulose acetate succinate, hydroxypropylmethyl cellulose phthalate, vinylpyrrolidone-vinyl acetate copolymers, piperonyl butoxide, glucose, pregelatinized starch, fumaric acid, fumaric acid-stearic acid-polyvinyl acetal diethylaminoacetate-hydroxypropylmethyl cellulose 2910 mixtures, pullulan, povidone, polyvinyl alcohol (completely saponified product), polyvinyl alcohol (partially saponified product), sodium polyphosphate, macrogol 4000, macrogol 6000, macrogol 20000, D-mannitol, or methylcellulose. Examples of preferred binders contained in the pharmaceutical composition of the present invention include carboxyvinyl polymers, hydroxypropyl methylcellulose acetate succinate, and povidone.

Examples of lubricants include, but are not limited to, cocoa fat, carnauba wax, hydrous silicon dioxide, dry aluminum hydroxide gel, glycerin fatty acid ester, magnesium silicate, light anhydrous silicic acid, crystalline cellulose, hardened oil, synthetic aluminum silicate, white beeswax, magnesium oxide, sodium potassium tartrate, sucrose fatty acid ester, stearic acid, calcium stearate, magnesium stearate, stearyl alcohol, polyoxyl 40 stearate, cetanol, soybean hardened oil, gelatin, talc, magnesium carbonate, precipitated calcium carbonate, corn starch, potato starch, fumaric acid, stearyl sodium fumarate, macrogol 600, macrogol 4000, macrogol 6000, beeswax, magnesium metasilicate aluminate, sodium laurate, or magnesium sulfate. Preferably, at least one or more lubricants contained in the pharmaceutical composition of the present invention are organic acids and/or salts thereof. Examples of preferred lubricants contained in the pharmaceutical composition of the present invention include stearyl sodium fumarate.

Examples of fluidizing agents include, but are not limited to, hydrous silicon dioxide, light anhydrous silicic acid, crystalline cellulose, synthetic aluminum silicate, titanium oxide, stearic acid, calcium stearate, magnesium stearate, calcium tertiary phosphate, talc, corn starch, or magnesium aluminometasilicate.

Examples of coloring agents can include, but are not limited to, yellow iron sesquioxide, iron sesquioxide, titanium oxide, orange essence, brown iron oxide, β-carotene, black iron oxide, food blue No. 1, food blue No. 2, food red No. 2, food red No. 3, food red No. 102, food yellow No. 4, or food yellow No. 5.

Examples of polishing agents include, but are not limited to, carnauba wax, hardened oil, a polyvinyl acetate resin, white beeswax, titanium dioxide, stearic acid, calcium stearate, polyoxyl 40 stearate, magnesium stearate, purified shellac, purified paraffin/carnauba wax mixture, cetanol, talc, colored silver foil, white shellac, paraffin, povidone, macrogol 1500, macrogol 4000, macrogol 6000, beeswax, glycerin monostearate, or rosin. The polishing agent is preferably carnauba wax, titanium dioxide, or talc.

The dosage form of the pharmaceutical composition of the present invention may be a dosage form that can be orally administered or a dosage form that can be parenterally administered without particular limitations, and is preferably a dosage form that can be orally administered.

The dosage form that can be orally administered may be a solid formulation or a nonsolid formulation without particular limitations, and is preferably a solid formulation.

The solid formulation that can be orally administered is not particularly limited, and is preferably in the form of a tablet (including orally disintegrating tablets), granules (including fine granules), powder, or a capsule, more preferably in the form of a tablet or a capsule, even more preferably in the form of a tablet. The solid formulation that can be orally administered may be produced through widely known production methods.

When the pharmaceutical composition of the present invention is in the dosage form of granules, the granules may be produced through blending compound I or a pharmacologically acceptable salt thereof, or a solvate thereof with an acid or a salt thereof, a sugar alcohol and/or a water-swelling additive, and optional additives such as an excipient, a binder, a disintegrant, and other appropriate members, and granulating the thus-obtained uniform mixture through an appropriate technique. Additionally, the thus-produced granules may be coated with a coating agent by means of a fluidized bed coater through spraying a suspension/solution of the coating agent onto the granules.

Alternatively, when the pharmaceutical composition of the present invention is in the dosage form of a powder, the powder or microgranules may be produced through blending compound I or a pharmacologically acceptable salt thereof, or a solvate thereof with an acid or a salt thereof, a sugar alcohol and/or a water-swelling additive and optional additives such as an excipient, a binder, a disintegrant, and other appropriate members, to form a uniform admixture, and pulverizing or micro-granulating the thus-obtained admixture through an appropriate technique. Additionally, the thus-produced powder or microgranules may be coated with a coating agent by means of a fluidized bed coater through spraying a suspension/solution of the coating agent onto the powder or microgranules.

Alternatively, when the pharmaceutical composition of the present invention is in the dosage form of a capsule, the aforementioned granules or powders may be encapsulated with coating capsules.

When the pharmaceutical composition of the present invention is in the dosage form of a tablet, tablets may be produced directly through compression molding of a powder mixture containing compound I or a pharmacologically acceptable salt thereof, or a solvate thereof and acceptable additives for pharmaceuticals. Alternatively, the tablets may be produced through granulating a powder mixture containing compound I or a pharmacologically acceptable salt thereof, or a solvate thereof and acceptable additives for pharmaceuticals, through a technique such as fluidized-bed granulation or high-shear granulation, followed by compression molding of the formed granules. The pressure of compression molding may be determined within an appropriate range, so long as the effect of the present invention is not impaired. The compression molding is preferably performed at, for example, 5 to 30 kN, preferably 6 to 29 kN. When the pharmaceutical composition of the present invention is in the dosage form of a tablet, tablet density is not particularly limited, for example, 1.1 to 1.5 mg/mm$^3$, preferably 1.2 to 1.4 mg/mm$^3$. Moreover, examples of the shape of the tablet include, but not particularly limited to, lens, disc, round, oval (e.g., caplets), polygonal (e.g., triangle or rhombus), and teardrop shapes. Furthermore, the produced tablet may be further coated with a coating agent by means of a pan coater through spraying a suspension/solution of the coating agents onto the tablets.

When the pharmaceutical composition of the present invention is a tablet or a capsule, compound I or the pharmacologically acceptable salt thereof, or the solvate thereof, and the acid or the salt thereof may be contained within the same granules. Alternatively, the pharmaceutical composition of the present invention may assume a form in which compound I or the pharmacologically acceptable salt thereof, or the solvate thereof is contained within granules and the organic acid or the salt thereof is contained outside the granules.

When the pharmaceutical composition of the present invention is a solid formulation, the solid formulation may comprise a coating agent. The coated solid formulation is not limited to coated solid formulations such as coated tablets and encompasses various solid formulations comprising coating agents. For example, a solid formulation containing compound I or the pharmacologically acceptable salt thereof, or the solvate thereof, wherein coating agents are formulated in a matrix form in the solid formulation is also included in the present invention.

Examples of the coating agent can include coating agents generally employed in pharmaceutical manufacturing for coating tablets and granules therewith. Preferably, the coating agent has low solubility within the pH range in the intestine. Specifically, a coating agent which is difficult to dissolve within the pH range in the intestine is generally preferred, as compared with an enteric coating agent. Examples of preferred coating agents include: cellulose derivatives such as hypromellose (hydroxypropyl methylcellulose), hydroxypropyl cellulose, ethyl cellulose, and methyl cellulose; polyvinyl compounds such as polyvinyl alcohol, povidone (polyvinylpyrrolidone), polyvinyl acetal diethylaminoacetate, and vinyl acetate resins; acrylate derivatives such as aminoalkyl methacrylate copolymer RS and ethyl acrylate-methyl methacrylate copolymer dispersion; saccharides such as sucrose and mannitol; and combinations thereof. Preferred examples of coating agents include hypromellose, ethyl cellulose, polyvinyl alcohol, and their combinations. More preferred examples thereof include hypromellose.

In the present invention, the aforementioned coating agent and other additives required for preparing a coating suspension (e.g., a plasticizer) may be incorporated in combination into the composition. Examples of the additives required for preparing a coating suspension (e.g., plasticizer) include macrogols (polyethylene glycols having an average molecular weight of 1,000 to 35,000) such as macrogol 1000, macrogol 1500, macrogol 1540, macrogol 4000, macrogol 6000, macrogol 8000, macrogol 20000, and macrogol 35000, glycerin fatty acid ester, sucrose fatty acid ester, castor oil, triethyl citrate, triacetin, and talc. The aforementioned coating agents may further contain the aforementioned coloring agent, and the mixture may be incorporated into the pharmaceutical composition of the present invention.

The pharmaceutical composition of the present invention contains 0.5 to 20% by weight, preferably 1.0 to 15% by weight, more preferably 1.5 to 10% by weight of the coating agents.

In the present invention, the solid formulation containing compound I or a pharmacologically acceptable salt thereof, or a solvate thereof may be coated with the aforementioned coating agent through a widely known coating process for solid formulation coating. No particular limitation is imposed on the coating process, and for example, there may be employed a spray coating process in which a solution/dispersion of the coating agent is sprayed onto a solid formulation containing compound I or a pharmacologically acceptable salt thereof, or a solvate thereof by means of a fluidized bed coater or a pan coater, a dip coating process in which a solid formulation containing compound I or a pharmacologically acceptable salt thereof, or a solvate thereof is dipped in a coating suspension; and a dry coating process employing impact in a gas flow. The solid formulation containing compound I or a pharmacologically acceptable salt thereof, or a solvate thereof which has not been subjected to the coating process may be produced through a conventionally known process.

The amount of compound I or the pharmacologically acceptable salt thereof, or the solvate thereof contained in one unit of the pharmaceutical composition is usually in the range of 1 mg to 200 mg, preferably 5 mg to 100 mg, 5 mg to 90 mg, 5 mg to 80 mg, 5 mg to 75 mg, 5 mg to 70 mg, or 5 mg to 60 mg, more preferably 15 mg to 60 mg, in terms of the free form of compound I.

The dissolution property of compound I or a pharmacologically acceptable salt thereof, or a solvate thereof of the pharmaceutical composition of the present invention can be evaluated by, for example, dissolution tests disclosed in the Japanese Pharmacopoeia, the United States Pharmacopoiea (USP), and the European Pharmacopoeia. Examples of the test medium employed in the dissolution tests will be described.

Non-limiting examples of the aforementioned strongly acidic dissolution medium include the JP 1st fluid described in the Japanese Pharmacopoeia; and "USP 0.1N HCl, Simulated Gastric Fluid without Enzyme" described in the United States Pharmacopoeia.

Non-limiting examples of the dissolution test medium (pH 6.8) include the JP 2nd fluid and phosphate buffer (pH 6.8) described in the Japanese Pharmacopoeia, "USP Phosphate Buffer (pH 6.8)", Simulated Intestinal Fluid without Enzyme described in the United States Pharmacopoeia, and Phosphate Buffer Solution (pH 6.8) described in the European Pharmacopoeia.

Moreover, dissolution test media (pH 3 to 5) may be a test medium having a pH 4.0 or pH 4.5. Specific examples include acetic acid-sodium acetate buffer described in the Japanese Pharmacopoeia, "USP Acetate Buffer" described in the United States Pharmacopoeia, and Acetate Buffer Solution (pH 4.5) described in the European Pharmacopoeia. Moreover, a diluted McIlvaine buffer of pH 4.0 may also be used. However, the dissolution test medium of pH 3 to 5 is not limited to the above examples.

These dissolution test media are prepared through methods described in the corresponding pharmacopoeia or the like of each country. When the employed dissolution test medium is a buffer solution, variation of the pH of the test medium is preferably within ±0.05 of pH defined for each dissolution medium.

When the pharmaceutical composition of the present invention is subjected to a dissolution test according to the method described in the dissolution test method of the Japanese Pharmacopoeia (paddle method; at a rotation speed of 50 rpm), the composition exhibits an average percentage dissolution of compound I, in a dissolution test medium having a pH of 6.8, of 70% or higher in 45 minutes after the start of the dissolution test, preferably of 75% or higher in 45 minutes after the start, even more preferably of 80% or higher in 45 minutes after the start.

Moreover, when the pharmaceutical composition of the present invention is subjected to a dissolution test according to the method described in the dissolution test method of the Japanese Pharmacopoeia (paddle method; at a rotation speed of 50 rpm), the composition exhibits an average percentage dissolution of compound I, in a dissolution test medium having a pH of 4.5, preferably of 85% or higher in 30 minutes after the start of the dissolution test, more preferably of 85% in 15 minutes after the start.

The pharmaceutical composition of the present invention exhibits a high inhibitory effect on activated blood coagulation factor X (FXa) and as such, is useful as an anticoagulant agent or an agent for preventing and/or treating thrombosis or embolism. The pharmaceutical composition of the present invention is useful as a pharmaceutical drug for mammals including humans, an activated blood coagulation factor X inhibitor, an anticoagulant agent, an agent for preventing and/or treating thrombosis and/or embolism, an agent for preventing and/or treating thrombotic diseases, and further, an agent for preventing (in the present specification, the prevention includes secondary prevention) and/or treating cerebral infarction, cerebral embolism, pulmonary infarction, pulmonary embolism, myocardial infarction, angina pectoris, thrombus and/or embolism accompanying nonvalvular atrial fibrillation (NVAF), deep vein thrombosis, deep vein thrombosis after surgery, thrombosis after prosthetic valve/joint replacement, thromboembolism after total hip replacement (THR), thromboembolism after total knee replacement (TKR), thromboembolism after hip fracture surgery (HFS), thrombosis and/or reocclusion after revascularization, Buerger's disease, disseminated intravascular coagulation syndrome, systemic inflammatory response syndrome (SIRS), multiple organ dysfunction syndrome (MODS), thrombosis at the time of extracorporeal circulation, or blood coagulation at the time of blood collection.

Next, the present invention will be described in detail with reference to Examples. However, the present invention is not intended to be limited to these in any way.

EXAMPLES

In the present Examples, the dissolution property was tested according to the second method (paddle method; 50 rpm) described in the Japanese Pharmacopoeia. The dissolution amount was calculated as an average percentage dissolution of 6 tablets. The dissolution medium used was phosphate buffer of pH 6.8 (USP Phosphate buffer (pH 6.8)).

The following ingredients were used in the present Examples: excipient: D-mannitol (manufactured by Roquette Corp. (trade name: Pearitol 50C) and pregelatinized starch (manufactured by Asahi Kasei Chemicals Corp. (trade name: PCS PC-10)), disintegrant: crospovidone (manufactured by ISP (trade name: Polyplasdone INF-10)), carmellose (manufactured by Gotoku Chemical Co., Ltd. (trade name: NS-300)), croscarmellose sodium (manufactured by FMC Biopolymer (trade name: Ac-Di-Sol)), carmellose calcium (manufactured by Gotoku Chemical Co., Ltd. (trade name: ECG-505)), or sodium carboxymethyl starch (manufactured by JRS Pharma (trade name: EXPLOTAB)), binder: hydroxypropyl cellulose (manufactured by Nippon Soda Co., Ltd. (trade name: HPC-L)), pH adjuster: fumaric acid (manufactured by Wako Pure Chemical Industries, Ltd. or manufactured by Merck KGaA) or ascorbic acid (manufactured by F. Hoffmann-La Roche Ltd.), lubricant: magnesium stearate (manufactured by Mallinckrodt Company) or stearyl sodium fumarate (manufactured by JRS Pharma (trade name: PRUV)), and coating agent: a premix product containing hypromellose as a main component [OPADRY03F42132 or OPADRY03F430000 (trade name)].

Example 1

Example 1A

Ingredients shown in Table 1A, except for hydroxypropyl cellulose and magnesium stearate, were mixed, and the mixture was granulated by use of a fluidized bed granulating dryer after spraying of aqueous hydroxypropyl cellulose solution thereon. The thus-produced granules were mixed with magnesium stearate, to thereby yield granules which were compressed into tablets (13.3×8.2 mm, teardrop punch and die, compression pressure: approximately 13 kN) by use of a tableting machine (VIRGO, manufactured by Kikusui Seisakusho Ltd.). In this way, uncoated tablets having a density of approximately 1.25 mg/mm$^3$ were obtained.

TABLE 1A

|  |  | Formulation | | |
|---|---|---|---|---|
|  |  | A | B | C |
| Ingredient (mg) | Compound Ia | 80.8 | 80.8 | 80.8 |
|  | (in terms of compound I) | (60.0) | (60.0) | (60.0) |
|  | D-mannitol | 195.6 | 160.7 | 189.7 |
|  | Pregelatinized starch | 84.0 | 68.9 | 81.3 |
|  | Crospovidone | 21.4 | 21.4 | — |
|  | Fumaric acid | — | 50.0 | — |
|  | Carmellose | — | — | 30.0 |
|  | Hydroxypropyl cellulose | 12.2 | 12.2 | 12.2 |
|  | Magnesium stearate | 6.0 | 6.0 | 6.0 |
| Weight of uncoated tablet (mg) | | 400.0 | 400.0 | 400.0 |

FIG. 1A shows the results of the dissolution test on the uncoated tablets of each formulation in a phosphate buffer having a pH of 6.8. The tablets of formulation B supplemented with fumaric acid and the tablets of formulation C supplemented with carmellose instead of crospovidone were improved in their dissolution property at pH 6.8, as compared with the tablets of formulation A.

Furthermore, film-coated tablets were produced by use of a commercially available coating agent and a pan coater (DRC-200, manufactured by Powrex Corp.). A premix product containing hypromellose as a main component [OPADRY03F42132 (trade name)] was used in an amount of 20 mg as the coating agent.

Figure 2A:
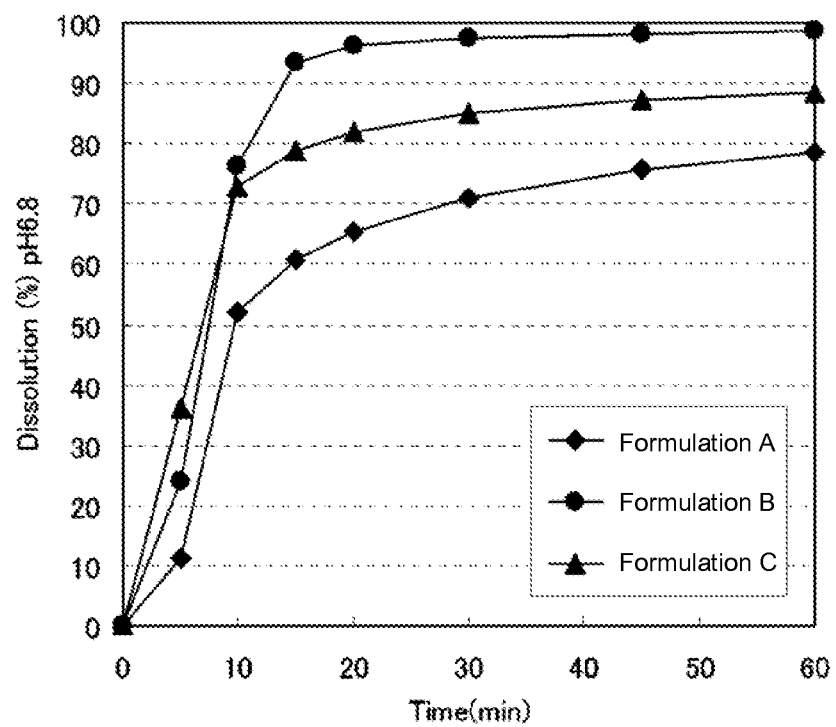
FIG. 2A is a diagram showing the dissolution property of compound I in the neutral range for film-coated tablets having formulations A to C. The vertical axis shows the dissolution amount of compound I, and the horizontal axis shows time (min).

FIG. 2A shows the results of the dissolution test on the film-coated tablets of each formulation in a phosphate buffer having a pH of 6.8. The film-coated tablets of formulations B and C supplemented with fumaric acid or carmellose were also improved in their dissolution property at pH 6.8, as compared with the tablets of formulation A.

Example 1B

Ingredients shown in Table 1B, except for hydroxypropyl cellulose and magnesium stearate, were mixed, and the mixture was granulated by use of a fluidized bed granulating dryer after spraying of aqueous hydroxypropyl cellulose solution thereon. The thus-produced granules were mixed with magnesium stearate, to thereby yield granules which were compressed into tablets (formulation A: 13.3×8.2 mm, teardrop punch and die, compression pressure: approximately 13 kN; and formulations L to N: tablet diameter: 10.5 mmφ, round punch and die, compression pressure: approximately 10 kN) by use of a tableting machine (VIRGO or 18HUK, manufactured by Kikusui Seisakusho Ltd.). In this way, uncoated tablets having a density of approximately 1.25 mg/mm$^3$ were obtained.

TABLE 1B

|  |  | Formulation | | | |
|---|---|---|---|---|---|
|  |  | A | L | M | N |
| Ingredient (mg) | Compound Ia | 80.8 | 80.8 | 80.8 | 80.8 |
|  | (in terms of compound I) | (60.0) | (60.0) | (60.0) | (60.0) |
|  | D-mannitol | 195.6 | 162.7 | 199.8 | 199.8 |

TABLE 1B-continued

|  | Formulation | | | |
|---|---|---|---|---|
|  | A | L | M | N |
| Pregelatinized starch | 84.0 | 69.7 | 84.0 | 84.0 |
| Crospovidone | 21.4 | 21.4 | — | — |
| Ascorbic acid | — | 50.0 | — | — |
| Croscarmellose sodium | — | — | 20.0 | — |
| Carmellose calcium | — | — | — | 20.0 |
| Hydroxypropyl cellulose | 12.2 | 12.2 | 12.2 | 12.2 |
| Magnesium stearate | 6.0 | 3.2 | 3.2 | 3.2 |
| Weight of uncoated tablet (mg) | 400.0 | 400.0 | 400.0 | 400.0 |

Figure 1B:
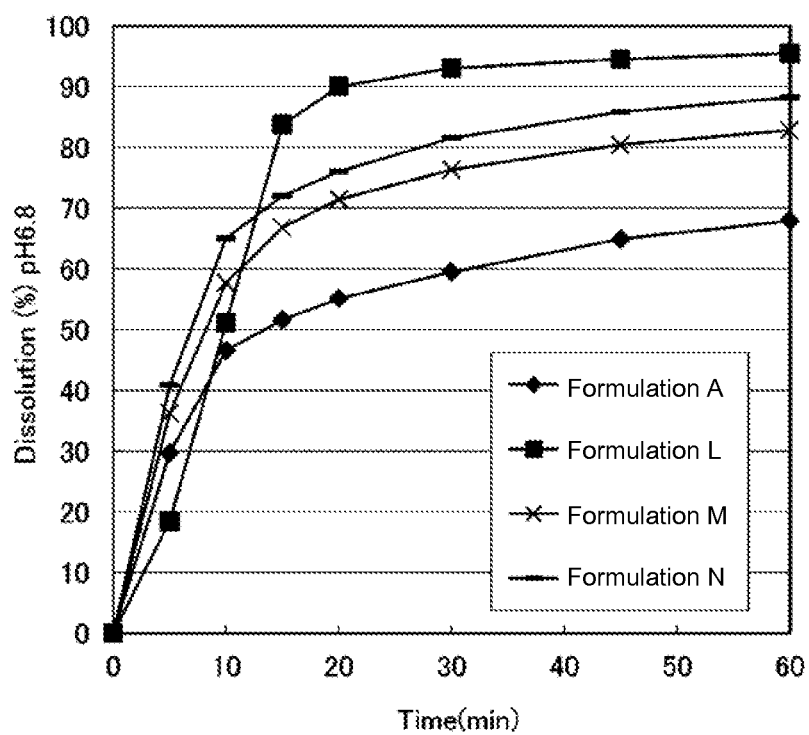
FIG. 1B is a diagram showing the dissolution property of compound I in the neutral range for uncoated tablets having formulations A and L to N. The vertical axis shows the dissolution amount of compound I, and the horizontal axis shows time (min).

FIG. 1B shows the results of the dissolution test on the uncoated tablets of each formulation in a phosphate buffer having a pH of 6.8. The tablets of formulation L supplemented with ascorbic acid and the tablets of formulations M and N supplemented with croscarmellose sodium and carmellose calcium, respectively, instead of crospovidone were improved in their dissolution property at pH 6.8, as compared with the tablets of formulation A.

Furthermore, film-coated tablets were obtained by use of 20 mg of OPADRY03F42132 (trade name) per uncoated tablet in the same way as in Example 1A.

Figure 2B:
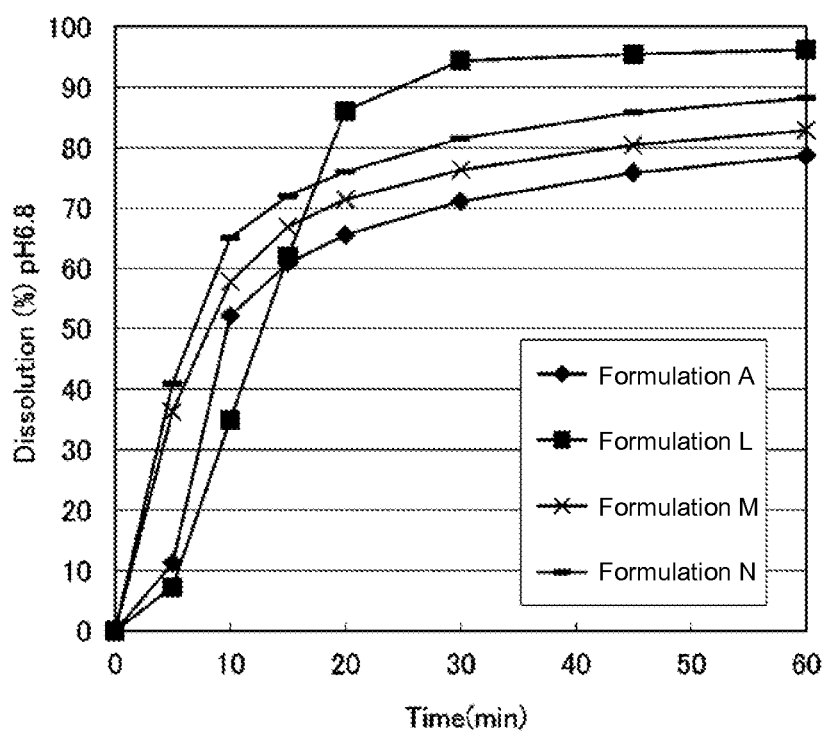
FIG. 2B is a diagram showing the dissolution property of compound I in the neutral range for film-coated tablets having formulations A and L to N. The vertical axis shows the dissolution amount of compound I, and the horizontal axis shows time (min).

FIG. 2B shows results of the dissolution test on the film-coated tablets of each formulation in a phosphate buffer having a pH of 6.8. The film-coated tablets of formulations L, M, and N supplemented with ascorbic acid, croscarmellose sodium, or carmellose calcium were also improved in their dissolution property at pH 6.8, as compared with the tablets of formulation A.

Figure 1C:
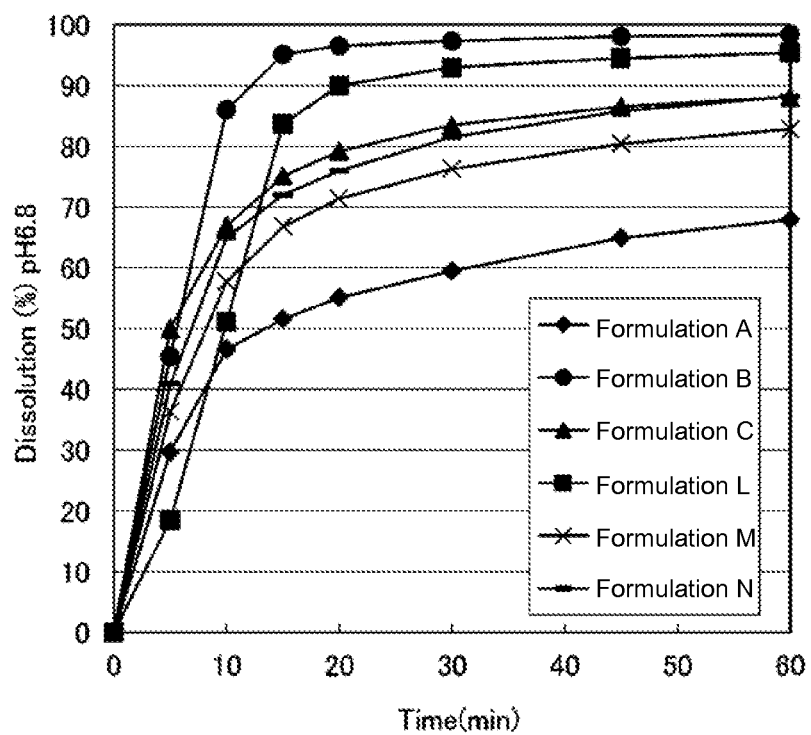
FIG. 1C is a diagram showing the dissolution property of compound I in the neutral range for uncoated tablets having formulations A to C and L to N. The vertical axis shows the dissolution amount of compound I, and the horizontal axis shows time (min).
Figure 2C:
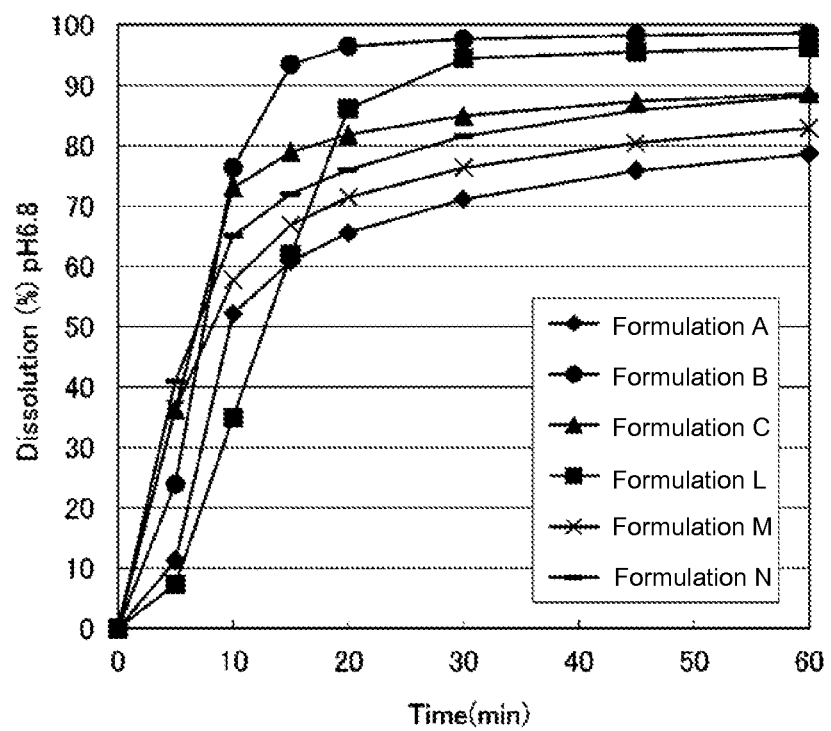
FIG. 2C is a diagram showing the dissolution properties of compound I in the neutral range for film-coated tablets having formulations A to C and L to N. The vertical axis shows the dissolution amount of compound I, and the horizontal axis shows time (min).

The results of the dissolution test on the uncoated tablets obtained in Examples 1A and 1B in a phosphate buffer having a pH of 6.8 are summarized in FIG. 1C. The results of the dissolution test on the coated tablets obtained in Examples 1A and 1B in a phosphate buffer having a pH of 6.8 are summarized in FIG. 2C.

Example 2

Example 2A

Ingredients shown in Table 2A, except for hydroxypropyl cellulose, croscarmellose sodium, carmellose calcium, and magnesium stearate, were mixed, and the mixture was granulated by use of a fluidized bed granulating dryer after spraying of aqueous hydroxypropyl cellulose solution thereon. For formulation D, the thus-produced granules were mixed with only magnesium stearate while the granules for formulation E or F were mixed with magnesium stearate as well as croscarmellose sodium or carmellose calcium, to thereby yield granules which were compressed into tablets (tablet diameter: 11.0 mmφ, round punch and die, compression pressure: approximately 14 kN) by use of a tableting machine (VIRGO, manufactured by Kikusui Seisakusho Ltd.). In this way, uncoated tablets having a density of approximately 1.25 mg/mm$^3$ were obtained.

TABLE 2A

|  |  | Formulation | | |
|---|---|---|---|---|
|  |  | D | E | F |
| Ingredient (mg) | Compound Ia | 80.8 | 80.8 | 80.8 |
|  | (in terms of compound I) | (60.0) | (60.0) | (60.0) |
|  | D-mannitol | 198.4 | 198.4 | 198.4 |

TABLE 2A-continued

|  | Formulation | | |
|---|---|---|---|
|  | D | E | F |
| Pregelatinized starch | 84.0 | 84.0 | 84.0 |
| Crospovidone | 21.4 | 21.4 | 21.4 |
| Hydroxypropyl cellulose | 12.2 | 12.2 | 12.2 |
| Croscarmellose sodium | — | 20.0 | — |
| Carmellose calcium | — | — | 20.0 |
| Magnesium stearate | 3.2 | 3.2 | 3.2 |
| Weight of uncoated tablet (mg) | 400.0 | 420.0 | 420.0 |

Figure 3A:
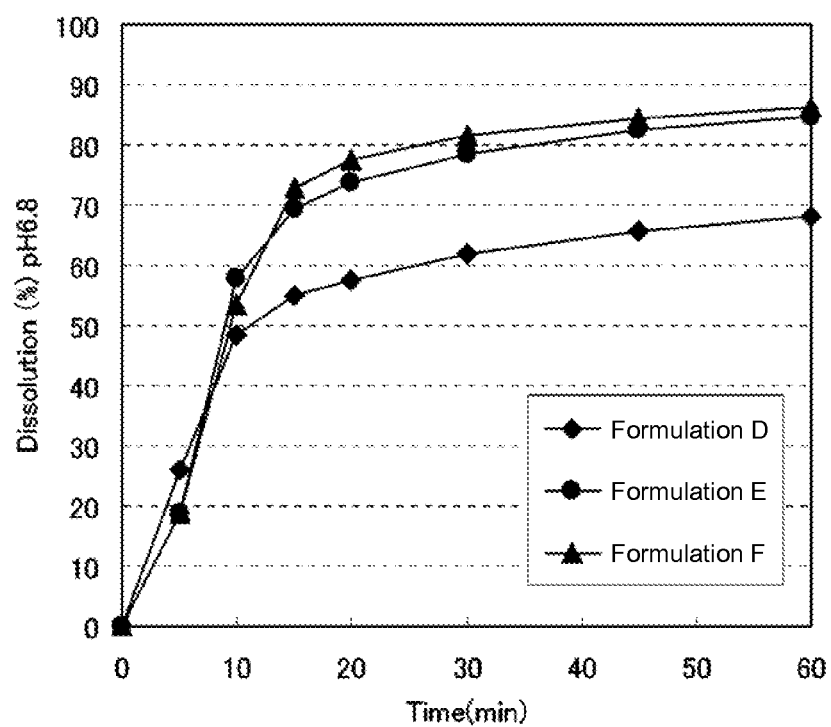
FIG. 3A is a diagram showing the dissolution property of compound I in the neutral range for uncoated tablets having formulations D to F. The vertical axis shows the dissolution amount of compound I, and the horizontal axis shows time (min).

FIG. 3A shows the results of the dissolution test on the uncoated tablets of each formulation in a phosphate buffer having a pH of 6.8. The tablets of formulations E and F supplemented with croscarmellose sodium or carmellose calcium were improved in their dissolution property at pH 6.8, as compared with the tablets of formulation D.

Furthermore, film-coated tablets were obtained by use of 20 mg of OPADRY03F430000 (trade name) per uncoated tablet in the same way as in Example 1A.

Figure 4A:
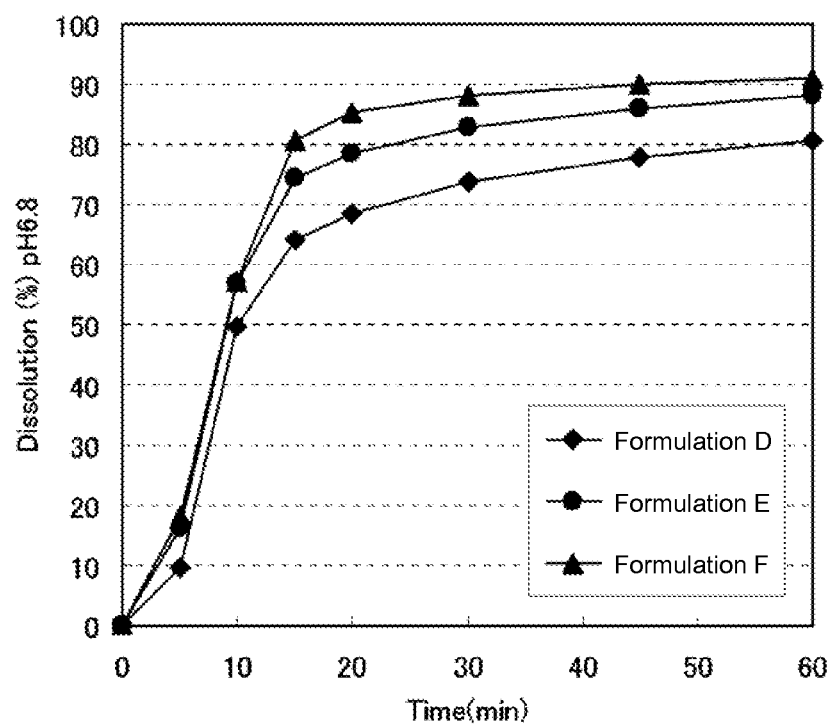
FIG. 4A is a diagram showing the dissolution property of compound I in the neutral range for film-coated tablets having formulations D to F. The vertical axis shows the dissolution amount of compound I, and the horizontal axis shows time (min).

FIG. 4A shows the results of the dissolution test on the film-coated tablets of each formulation in a phosphate buffer having a pH of 6.8. The film-coated tablets of formulations E and F supplemented with croscarmellose sodium or carmellose calcium were also improved in their dissolution property at pH 6.8, as compared with the tablets of formulation D.

Example 2B

Ingredients shown in Table 2B, except for hydroxypropyl cellulose, carmellose, fumaric acid, ascorbic acid, and magnesium stearate, were mixed, and the mixture was granulated by use of a fluidized bed granulating dryer after spraying of aqueous hydroxypropyl cellulose solution thereon. For formulation D, the thus-produced granules were mixed with only magnesium stearate while the granules of formulation O, P, or Q were mixed with magnesium stearate as well as carmellose, fumaric acid, or ascorbic acid, to thereby yield granules which were compressed into tablets (formulation D: tablet diameter: 11.0 mmϕ, round punch and die, compression pressure: approximately 14 kN; and formulations O to Q: tablet diameter: 10.5 mmϕ, round punch and die, compression pressure: approximately 13 kN) by use of a tableting machine (VIRGO or 18HUK, manufactured by Kikusui Seisakusho Ltd.). In this way, uncoated tablets having a density of approximately 1.25 mg/mm$^3$ were obtained.

TABLE 2B

| | | Formulation | | | |
|---|---|---|---|---|---|
| | | D | O | P | Q |
| Ingredient (mg) | Compound Ia | 80.8 | 80.8 | 80.8 | 80.8 |
| | (in terms of compound I) | (60.0) | (60.0) | (60.0) | (60.0) |
| | D-mannitol | 198.4 | 198.4 | 198.4 | 198.4 |
| | Pregelatinized starch | 84.0 | 84.0 | 84.0 | 84.0 |
| | Crospovidone | 21.4 | 21.4 | 21.4 | 21.4 |
| | Hydroxypropyl cellulose | 12.2 | 12.2 | 12.2 | 12.2 |
| | Carmellose | — | 20.0 | — | — |
| | Fumaric acid | — | — | 50.0 | — |
| | Ascorbic acid | — | — | — | 50.0 |
| | Magnesium stearate | 3.2 | 3.2 | 3.2 | 3.2 |
| Weight of uncoated tablet (mg) | | 400.0 | 420.0 | 450.0 | 450.0 |

Figure 3B:
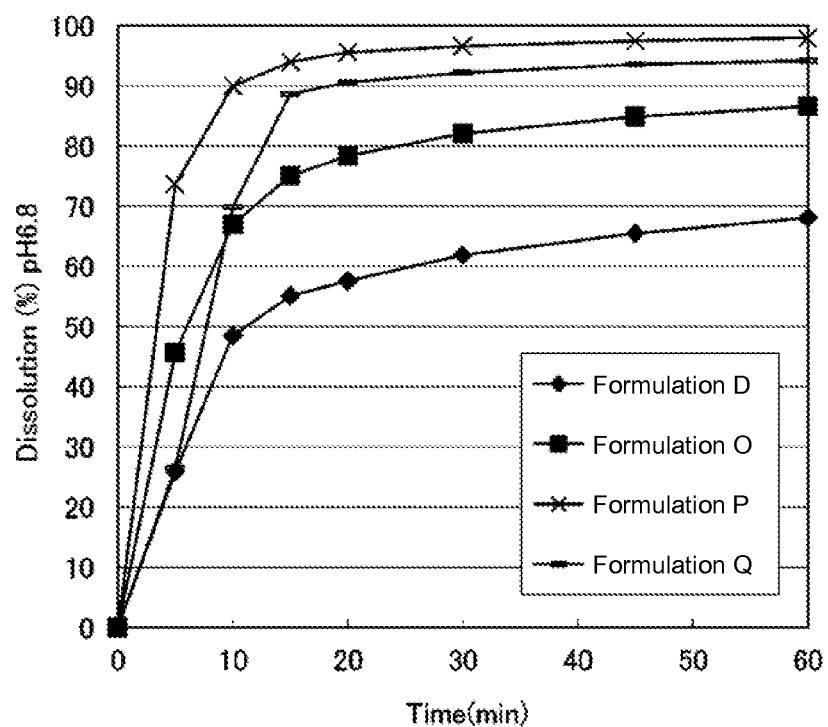
FIG. 3B is a diagram showing the dissolution property of compound I in the neutral range for uncoated tablets having formulations D and O to Q. The vertical axis shows the dissolution amount of compound I, and the horizontal axis shows time (min).

FIG. 3B shows the results of the dissolution test on the uncoated tablets of each formulation in a phosphate buffer having a pH of 6.8. The tablets of formulations O, P, and Q supplemented with carmellose, fumaric acid, or ascorbic acid were improved in their dissolution property at pH 6.8, as compared with the tablets of formulation D.

Furthermore, film-coated tablets were obtained by use of 20 mg of OPADRY03F42132 (trade name) or OPADRY03F430000 (trade name) per uncoated tablet in the same way as in Example 1A.

Figure 4B:
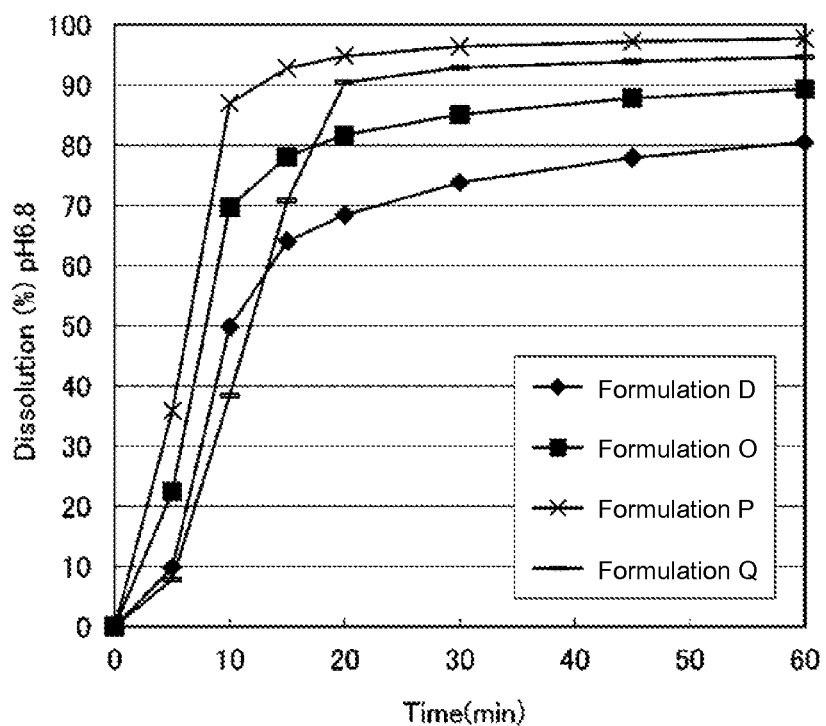
FIG. 4B is a diagram showing the dissolution property of compound I in the neutral range for film-coated tablets having formulations D and O to Q. The vertical axis shows the dissolution amount of compound I, and the horizontal axis shows time (min).

FIG. 4B shows results of the dissolution test on the film-coated tablets of each formulation in a phosphate buffer having a pH of 6.8. The film-coated tablets of formulations O, P, and Q supplemented with carmellose, fumaric acid, or ascorbic acid were also improved in their dissolution property at pH 6.8, as compared with the tablets of formulation D.

Figure 3C:
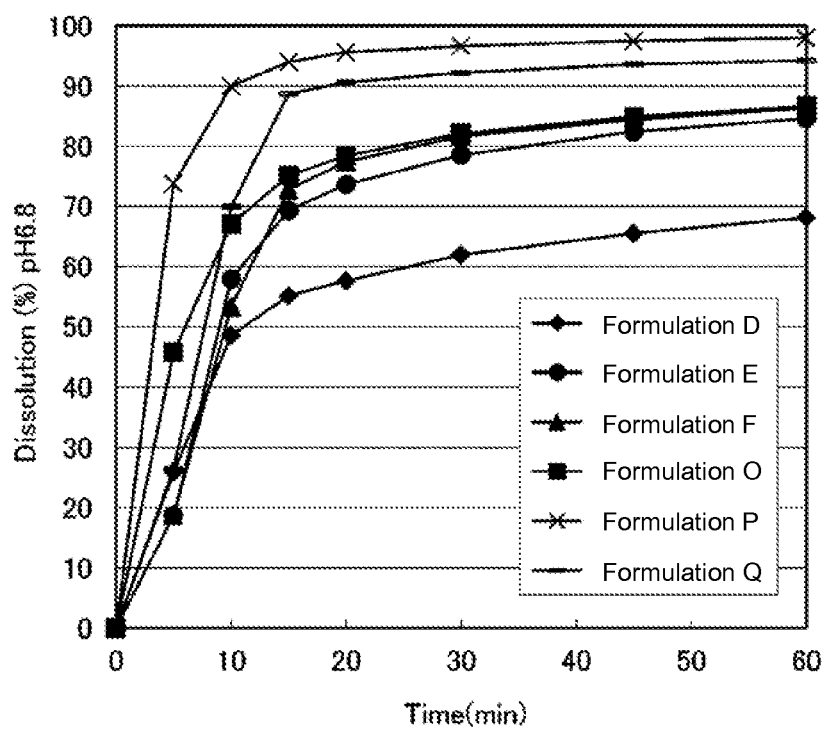
FIG. 3C is a diagram showing the dissolution property of compound I in the neutral range for uncoated tablets having formulations D to F and O to Q. The vertical axis shows the dissolution amount of compound I, and the horizontal axis shows time (min).
Figure 4C:
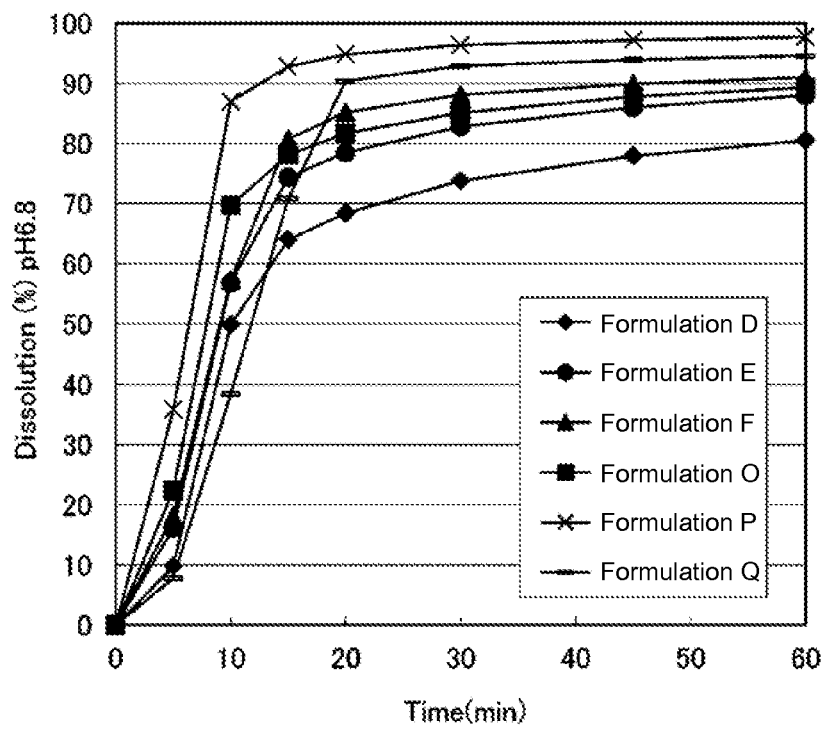
FIG. 4C is a diagram showing the dissolution property of compound I in the neutral range for film-coated tablets having formulations D to F and O to Q. The vertical axis shows the dissolution amount of compound I, and the horizontal axis shows time (min).

The results of the dissolution test on the uncoated tablets obtained in Examples 2A and 2B in a phosphate buffer having a pH of 6.8 are summarized in FIG. 3C. The results of the dissolution test on the coated tablets obtained in Examples 2A and 2B in a phosphate buffer having a pH of 6.8 are summarized in FIG. 4C.

Example 3

Ingredients shown in Table 3, except for hydroxypropyl cellulose and magnesium stearate, were mixed, and the mixture was granulated by use of a fluidized bed granulating dryer after spraying of aqueous hydroxypropyl cellulose solution thereon. The thus-produced granules were mixed with magnesium stearate, to thereby yield granules which were compressed into tablets (13.3×8.2 mm, teardrop punch and die, compression pressure: approximately 13 kN) by use of a tableting machine (VIRGO, manufactured by Kikusui Seisakusho Ltd.). In this way, uncoated tablets having a density of approximately 1.25 mg/mm$^3$ were obtained.

TABLE 3

| | | Formulation | |
|---|---|---|---|
| | | G | H |
| Ingredient (mg) | Compound Ia | 80.8 | 80.8 |
| | (in terms of compound I) | (60.0) | (60.0) |
| | D-mannitol | 195.6 | 196.7 |
| | Pregelatinized starch | 84.0 | 84.3 |
| | Crospovidone | 21.4 | — |
| | Sodium carboxymethyl starch | — | 20.0 |
| | Hydroxypropyl cellulose | 12.2 | 12.2 |
| | Magnesium stearate | 6.0 | 6.0 |
| Weight of uncoated tablet (mg) | | 400.0 | 400.0 |

Figure 5:
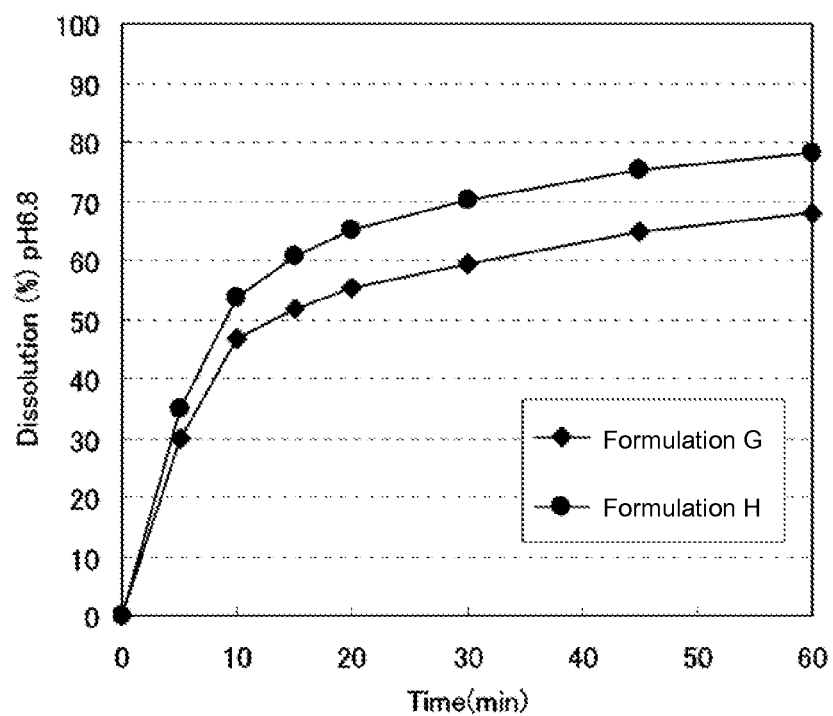
FIG. 5 is a diagram showing the dissolution property of compound I in the neutral range for uncoated tablets having formulations G and H. The vertical axis shows the dissolution amount of compound I, and the horizontal axis shows time (min).

FIG. 5 shows the results of the dissolution test on the uncoated tablets of each formulation in a phosphate buffer having a pH of 6.8. The tablets of formulation H were improved in their dissolution property at pH 6.8, as compared with the tablets of formulation G.

Furthermore, film-coated tablets were obtained by use of 20 mg of OPADRY03F42132 (trade name) per uncoated tablet in the same way as in Example 1A.

Figure 6:
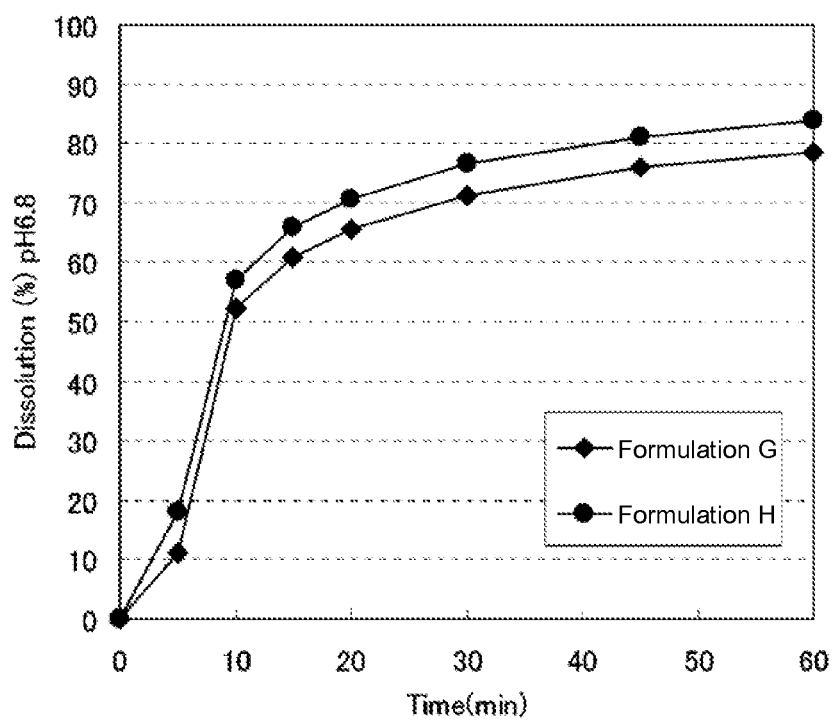
FIG. 6 is a diagram showing the dissolution property of compound I in the neutral range for film-coated tablets having formulations G and H. The vertical axis shows the dissolution amount of compound I, and the horizontal axis shows time (min).

FIG. 6 shows the results of the dissolution test on the film-coated tablets of each formulation in a phosphate buffer having a pH of 6.8. The film-coated tablets of formulation H supplemented with sodium carboxymethyl starch were also improved in their dissolution property at pH 6.8, as compared with the tablets of formulation G.

Example 4

Ingredients shown in Table 4, except for hydroxypropyl cellulose, magnesium stearate, and stearyl sodium fumarate, were mixed, and the mixture was granulated by use of a fluidized bed granulating dryer after spraying of aqueous hydroxypropyl cellulose solution thereon. The thus-produced granules were mixed with magnesium stearate or stearyl sodium fumarate, to thereby yield granules which were compressed into tablets (13.3×8.2 mm, teardrop punch and die, compression pressure: approximately 13 kN) by use of a tableting machine (VIRGO, manufactured by Kikusui Seisakusho Ltd.). In this way, uncoated tablets having a density of approximately 1.25 mg/mm$^3$ were obtained.

TABLE 4

|  |  | Formulation | |
|---|---|---|---|
|  |  | J | K |
| Ingredient (mg) | Compound Ia | 80.8 | 80.8 |
|  | (in terms of compound I) | (60.0) | (60.0) |
|  | D-mannitol | 195.6 | 198.4 |
|  | Pregelatinized starch | 84.0 | 84.0 |
|  | Crospovidone | 21.4 | 21.4 |
|  | Hydroxypropyl cellulose | 12.2 | 12.2 |
|  | Magnesium stearate | 6.0 | — |
|  | Stearyl sodium fumarate | — | 16.2 |
| Weight of uncoated tablet (mg) |  | 400.0 | 413.0 |

Figure 7:
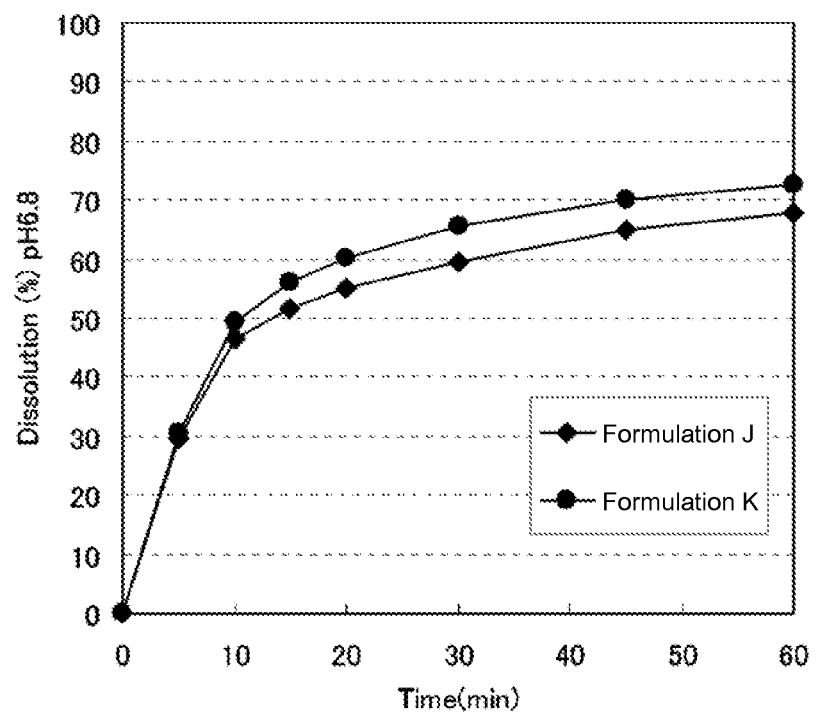
FIG. 7 is a diagram showing the dissolution property of compound I in the neutral range for uncoated tablets having formulations J and K. The vertical axis shows the dissolution amount of compound I, and the horizontal axis shows time (min).

FIG. 7 shows the results of the dissolution test on the uncoated tablets of each formulation in a phosphate buffer having a pH of 6.8. The tablets of formulation K were improved in their dissolution property at pH 6.8, as compared with the tablets of formulation J.

Furthermore, film-coated tablets were obtained by use of 20 mg of OPADRY03F42132 (trade name) per uncoated tablet in the same way as in Example 1A.

Figure 8:
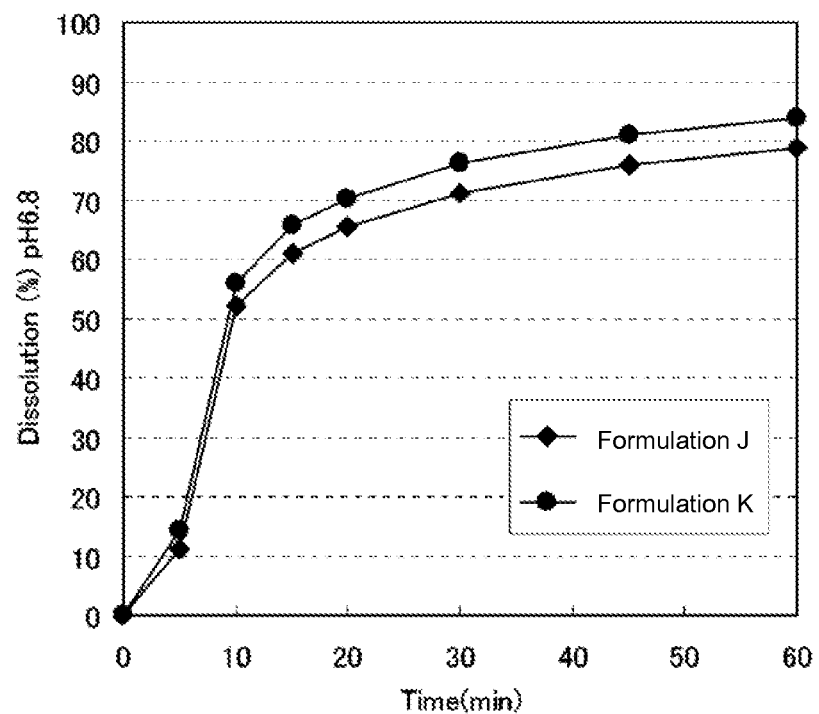
FIG. 8 is a diagram showing the dissolution property of compound I in the neutral range for film-coated tablets having formulations J and K. The vertical axis shows the dissolution amount of compound I, and the horizontal axis shows time (min).

FIG. 8 shows the results of the dissolution test on the film-coated tablets of each formulation in a phosphate buffer having a pH of 6.8. The film-coated tablets of formulation K were also improved in their dissolution property at pH 6.8, as compared with the tablets of formulation J.

Example 5

Ingredients shown in Table 5, except for hydroxypropyl cellulose, sodium carboxymethyl starch, and magnesium stearate, were mixed, and the mixture was granulated by use of a fluidized bed granulating dryer after spraying of aqueous hydroxypropyl cellulose solution thereon. For formulation R, the thus-produced granules were mixed with only magnesium stearate while the granules for formulation S were mixed with magnesium stearate as well as sodium carboxymethyl starch, to thereby yield granules which were compressed into tablets (formulation R: tablet diameter: 11.0 mmφ, round punch and die, compression pressure: approximately 14 kN; and formulation S: tablet diameter: 10.5 mmφ, round punch and die, compression pressure: approximately 12 kN) by use of a tableting machine (VIRGO or 18HUK, manufactured by Kikusui Seisakusho Ltd.). In this way, uncoated tablets having a density of approximately 1.25 mg/mm$^3$ were obtained.

TABLE 5

|  |  | Formulation | |
|---|---|---|---|
|  |  | R | S |
| Ingredient (mg) | Compound Ia | 80.8 | 80.8 |
|  | (in terms of compound I) | (60.0) | (60.0) |
|  | D-mannitol | 198.4 | 198.4 |

TABLE 5-continued

|  |  | Formulation | |
|---|---|---|---|
|  |  | R | S |
|  | Pregelatinized starch | 84.0 | 84.0 |
|  | Crospovidone | 21.4 | 21.4 |
|  | Hydroxypropyl cellulose | 12.2 | 12.2 |
|  | Sodium carboxymethyl starch | — | 20.0 |
|  | Magnesium stearate | 3.2 | 3.2 |
| Weight of uncoated tablet (mg) |  | 400.0 | 420.0 |

Figure 9:
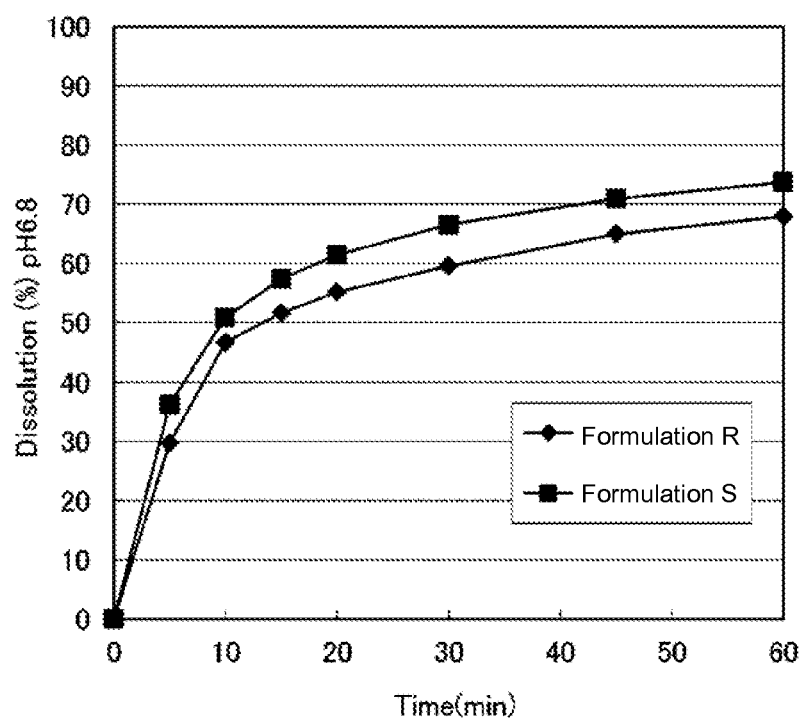
FIG. 9 is a diagram showing the dissolution property of compound I in the neutral range for uncoated tablets having formulations R and S. The vertical axis shows the dissolution amount of compound I, and the horizontal axis shows time (min).

FIG. 9 shows the results of the dissolution test on the uncoated tablets of each formulation in a phosphate buffer having a pH of 6.8. The tablets of formulation S supplemented with sodium carboxymethyl starch were improved in their dissolution property at pH 6.8, as compared with the tablets of formulation R.

Furthermore, film-coated tablets were obtained by use of 20 mg of OPADRY03F42132 (trade name) per uncoated tablet in the same way as in Example 1A.

Figure 10:
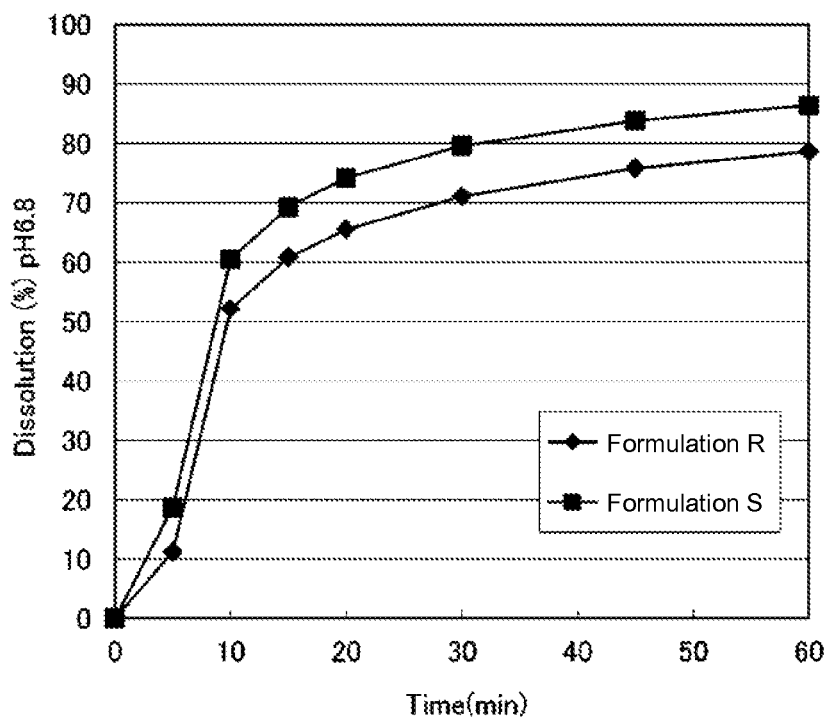
FIG. 10 is a diagram showing the dissolution property of compound I in the neutral range for film-coated tablets having formulations R and S. The vertical axis shows the dissolution amount of compound I, and the horizontal axis shows time (min).

FIG. 10 shows the results of the dissolution test on the film-coated tablets of each formulation in a phosphate buffer having a pH of 6.8. The film-coated tablets of formulation S supplemented with sodium carboxymethyl starch were also improved in their dissolution property at pH 6.8, as compared with the tablets of formulation R.

Example 6

Ingredients shown in Table 6, except for hydroxypropyl cellulose and magnesium stearate, were mixed, and the mixture was granulated by use of a fluidized bed granulating dryer after spraying of aqueous hydroxypropyl cellulose solution thereon. The thus-produced granules were mixed with magnesium stearate, to thereby yield granules. For formulation T, the granules were compressed into tablets (tablet diameter: 10.5 mmφ, round punch and die, compression pressure: approximately 6 kN (density: 1.15 mg/mm$^3$) and approximately 14 kN (density: 1.25 mg/mm$^3$)) by use of a tableting machine (VELA2 or AQU3 10362L2JII, manufactured by Kikusui Seisakusho Ltd.), to thereby yield uncoated tablets having a density of approximately 1.15 and approximately 1.25 mg/mm$^3$. For formulations U and V, the granules were compressed into tablets (tablet diameter: 13.3×8.2 mm, teardrop punch and die, compression pressure: approximately 8 kN (density: 1.15 mg/mm$^3$) and approximately 16 kN (density: 1.25 mg/mm$^3$)) by use of a tableting machine (VELA2 or AQU3 10362L2JII, manufactured by Kikusui Seisakusho Ltd.), to thereby yield uncoated tablets having a density of approximately 1.15 and approximately 1.25 mg/mm$^3$. Furthermore, film-coated tablets were obtained by use of 20 mg of OPADRY03F42132 (trade name) per uncoated tablet in the same way as in Example 1A.

TABLE 6

|  |  | Formulation | | |
|---|---|---|---|---|
|  |  | T | U | V |
| Ingredient (mg) | Compound Ia | 80.8 | 80.8 | 80.8 |
|  | (in terms of compound I) | (60.0) | (60.0) | (60.0) |
|  | D-mannitol | 198.4 | 181.7 | 198.0 |
|  | Pregelatinized starch | 84.0 | 77.9 | 85.0 |
|  | Crospovidone | 21.4 | 21.4 | — |
|  | Fumaric acid | — | 20.0 | — |
|  | Carmellose | — | — | 20.0 |

TABLE 6-continued

| | Formulation | | |
|---|---|---|---|
| | T | U | V |
| Hydroxypropyl cellulose | 12.2 | 12.2 | 12.2 |
| Magnesium stearate | 3.2 | 6.0 | 4.0 |
| Weight of uncoated tablet (mg) | 400.0 | 400.0 | 400.0 |

Figure 11:
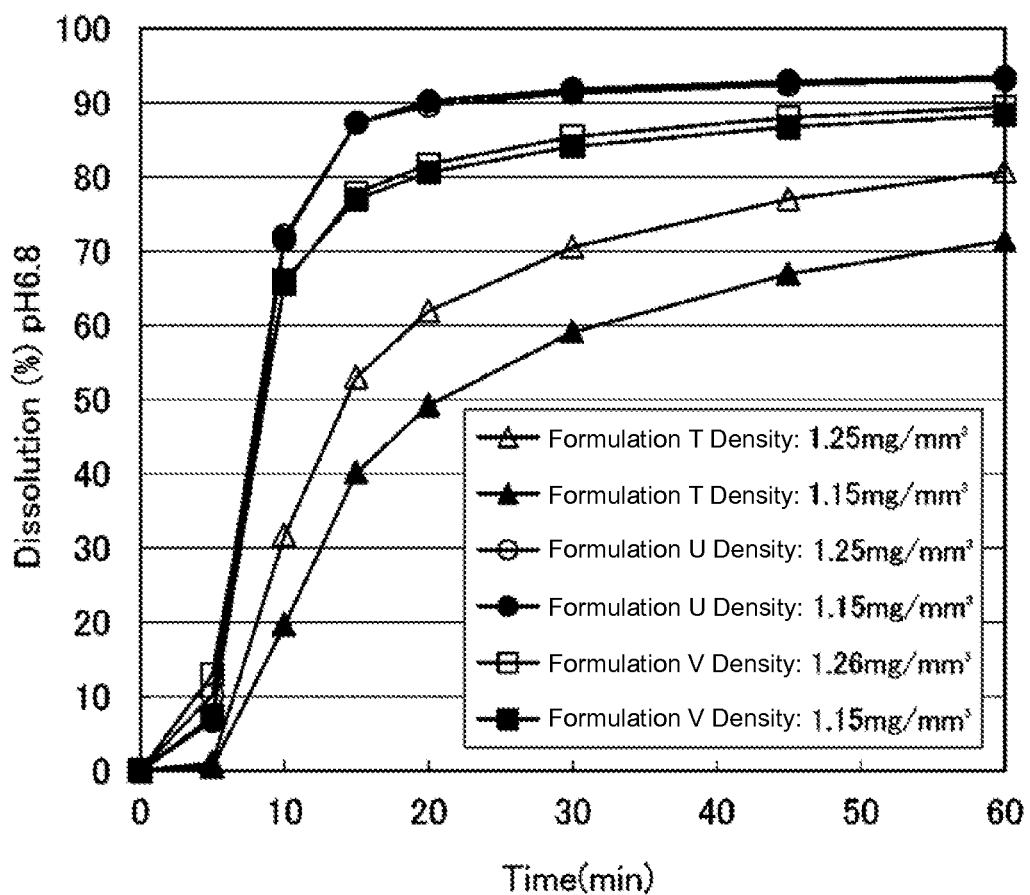
FIG. 11 is a diagram showing the dissolution property of compound I in the neutral range for film-coated tablets having formulations T to V. The vertical axis shows the dissolution amount of compound I, and the horizontal axis shows time (min).

FIG. 11 shows the results of the dissolution test on the film-coated tablets of each formulation in a phosphate buffer having a pH of 6.8. The tablets of formulations U and V supplemented with fumaric acid or carmellose were improved in their dissolution property at pH 6.8 without being influenced by tablet density, as compared with the tablets of formulation T.

The invention claimed is:

1. A solid formulation containing
    (A) an active ingredient consisting of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

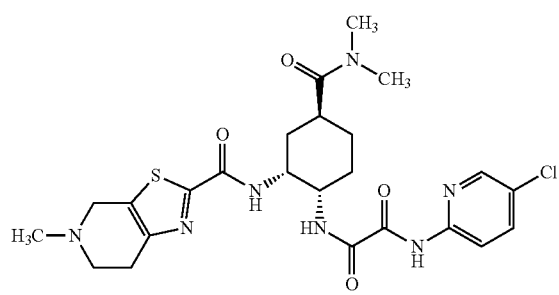

or a pharmacologically acceptable salt thereof, or a solvate thereof, and
    (B) fumaric acid,
    wherein the solid formulation, without a film-coating, exhibits an average percentage dissolution of compound I, in a dissolution test medium having a pH of 6.8, of 70% or higher in 45 minutes after the start of the dissolution test.

2. The solid formulation according to claim 1, wherein the solid formulation is in a dosage form of a tablet or capsule.

3. The solid formulation according to claim 1 further comprising carmellose.

4. The solid formulation according to claim 1, which is an immediate release tablet or a capsule.

5. The solid formulation according to claim 1, which comprises the component (A) and the component (B) within granules.

6. The solid formulation according to claim 1, which comprises the component (A) within granules and comprises the component (B) outside the granules.

7. The solid formulation according to claim 2, wherein the dosage form is a tablet.

8. The solid formulation according to claim 1, further comprising a sugar alcohol, a water-swelling additive, a disintegrant, a lubricant, and combinations thereof.

9. The solid formulation according to claim 1, wherein the solid formulation contains 40% to 60% by weight of a sugar alcohol.

10. The solid formulation according to claim 1, further comprising a sugar alcohol and a water-swelling additive in a ratio of 1.5 parts by weight of the water-swelling additive to 4 parts by weight of the sugar alcohol.

11. The solid formulation according to claim 1, further comprising a film-coating.

12. A solid formulation containing:
    (A) an active ingredient consisting of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

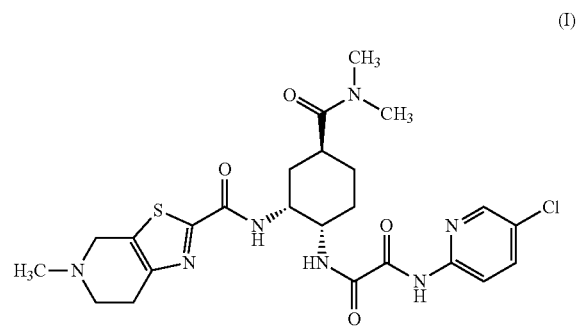 [SMILES: CN1CCc2nc(C(=O)N[C@@H]3C[C@@H](C(=O)N(C)C)CC[C@@H]3NC(=O)C(=O)Nc3ccc(Cl)cn3)sc2C1]

or a pharmacologically acceptable salt thereof, or a solvate thereof, and
    (B) fumaric acid;
    (C) a sugar alcohol;
    (D) a water-swelling additive;
    (E) a disintegrant; and
    (F) a lubricant,
    wherein the solid formulation, without a film-coating, exhibits an average percentage dissolution of compound I, in a dissolution test medium having a pH of 6.8, of 70% or higher in 45 minutes after the start of the dissolution test.

13. The solid formulation according to claim 12, wherein the solid formulation contains 40% to 60% by weight the sugar alcohol.

14. The solid formulation according to claim 12, wherein the ratio of water-swelling additive to sugar alcohol in the solid formulation is 1.5 parts by weight of the water-swelling additive to 4 parts by weight of the sugar alcohol.

15. The solid formulation according to claim 12, further comprising a film-coating.

16. The solid formulation according to claim 12, wherein the solid formulation is in a dosage form of a tablet.

* * * * *